United States Patent [19]

Burke et al.

[11] Patent Number: 4,880,734

[45] Date of Patent: * Nov. 14, 1989

[54] EUKARYOTIC REGULATABLE TRANSCRIPTION

[75] Inventors: Rae L. Burke, San Francisco; Steven Rosenberg, Oakland; Jeffrey R. Shuster, Walnut Creek; Patricia Tekamp-Olson; Pablo D. T. Valenzuela, both of San Francisco; Philip J. Barr, Orinda, all of Calif.

[73] Assignee: Chiron Corporation, Emeryville, Calif.

[*] Notice: The portion of the term of this patent subsequent to Oct. 24, 2006 has been disclaimed.

[21] Appl. No.: 868,639

[22] Filed: May 29, 1986

Related U.S. Application Data

[63] Continuation-in-part of Ser. No. 760,197, Jul. 29, 1985, which is a continuation-in-part of Ser. No. 468,589, Feb. 22, 1983, abandoned, and Ser. No. 609,540, May 11, 1984, abandoned.

[51] Int. Cl.$^4$ .................. C12P 21/00; C12P 21/02; C12N 5/00; C12N 15/00
[52] U.S. Cl. .................................. 435/68; 435/70; 435/172.3; 435/91; 435/320; 435/255; 435/256; 536/27; 935/28; 935/37; 935/41; 935/56; 935/60
[58] Field of Search .................. 435/68, 70, 91, 253, 435/255, 256, 172.3, 317.1, 320; 536/27; 935/28, 37, 41, 56, 60

[56] References Cited

U.S. PATENT DOCUMENTS 4,599,311 7/1986 Kawasaki ...................... 435/68
4,615,974 10/1985 Kingsman ...................... 435/68

FOREIGN PATENT DOCUMENTS 0073657 3/1983 European Pat. Off.
2154240 9/1985 United Kingdom ............ 435/68

OTHER PUBLICATIONS

Kramer et al. (1984) PNAS 81: 367–370.

Guarente et al. (1981) PNAS 79: 7401–7414.
Tuite et al. (1982) EMBOJ: 603–608.
V. Nussenzweig et al., Cell (1985) 42:401–03.
D. E. Arnot et al., Science (1985) 230: 815–18.
R. A. Kramer et al., Proc Nat Acad Sci U.S.A., (1984) 81: 367–70.
R. A. Hitzeman et al., Nuc Acids Res (1983) 11:2745–63.
A. Miyanohara et al., Proc Nat. Acad Sci U.S.A., (Jan., 1983) 80: 1–5.
L. Guarente et al., Proc Nat Acad Sci U.S.A., (Dec., 1982) 79: 7410–14.
G. Kawasaki et al., Biochem & Biophys Res Comm (1982) 108: 1107–12 (Kawasaki II).

(List continued on next page.)

Primary Examiner—Robin Teskin
Attorney, Agent, or Firm—Irell & Manella

[57] ABSTRACT

Methods and compositions are provided for efficient expression of genes in unicellular microorganisms, particularly yeast. The systems involve an expression system employing transcriptional initiation regions from glycolytic enzymes, particularly a chimeric expression system, having a first region providing for regulatable or constitutive expression, a second region providing for transcriptional initiation, where regions one and two are not found joined together in functional relationship in nature, and optionally a sequence providing for a secretory leader and processing signal, where the expression cassette will be joined to a gene which may be homologous or heterologous to the host. The expression cassette can be used on an extrachromosomal element or integrated into the host genome, whereby continuous expression can be achieved or inducible expression is obtained, by virtue of the presence or absence of an inducer. Constructions may be provided, where structural genes may be introduced in reading frame with the cassette to provide for expression of the natural peptide, a fused peptide, or a peptide precursor.

The S. cerevisiae strain AB110 (pAB24/P. vivax 1-5 was deposited at the A.T.C.C. on May 9, 1986, and given Accession No. 20797.

21 Claims, 12 Drawing Sheets

OTHER PUBLICATIONS

B. Meyhack et al., *EMBO J* (1982) 1: 675–80.
P. Valenzuela et al., *Nature* (1982) 298: 347–50.
M. F. Tuite et al, *EMBO J* (1982) 1: 603–08.
D. R. Beier et al., *Nature* (Dec., 1982) 300: 724–28.
M. J. Dobson et al., *Nuc Acids·Res* (1982) 10:2625–37.
K. Lerch et al., *J Biol Chem* (1981) 256: 11545–51.
R. A. Hitzeman et al., *Nature* (1981) 293: 717–22 (Hitzeman II).
J. R. Jabusch et al., *Biochem* (1980) 19:2310–16.
R. A. Hitzeman et al., *J Biol Chem* (1980) 255: 12073–80.
M. J. Holland et al., *J. Biol Chem.* (1979) 254: 5466–74.
P. K. Maitra et al., *J Biol Chem* (1971) 246: 475–88.
Tekamp-Olson et al., *Abstract: Cold Spring Harbor Meeting on "The Molecular Biology of Yeast"* (1983), p. 197.
Ptashne, *Nature* (1988) 335: 683–689.

promoter fragment

DNA 347

```
         10         20         30         40         50         60
AAGCTTACCA GTTCTCACAC GGAACACCAC TAATGGACAC AAATTCGAAA TACTTTGACC
         70         80         90        100        110        120
CTATTTTCGA GGACCTTGTC ACCTTGAGCC CAAGAGAGCC AAGATTTAAA TTTTCCTATG
        130        140        150        160        170        180
ACTTGATGCA AATTCCCAAA GCTAATAACA TGCAAGACAC GTACGGTCAA GAAGACATAT
        190        200        210        220        230        240
TTGACCTCTT AACTGGTTCA GACGCGACTG CCTCATCAGT AAGACCCGTT GAAAAGAACT
        250        260        270        280        290        300
TACCTGAAAA AAACGAATAT ATACTAGCGT TGAATGTTAG CGTCAACAAC AAGAAGTTTA
        310        320        330        340        350        360
ATGACGCGGA GGCCAAGGCA AAAAGATTCC TTGATTACGT AAGGGAGTTA GAATCATTTT
        370        380        390        400        410        420
GAATAAAAAA CACGCTTTTT CAGTTCGAGT TTATCATTAT CAATACTGCC ATTTCAAAGA
        430        440        450        460        470        480
ATACGTAAAT AATTAATAGT AGTGATTTTC CTAACTTTAT TTAGTCAAAA ATTAGCCTTT
        490        500        510        520        530        540
TAATTCTGCT GTAACCCGTA CATGCCCAAA ATAGGGGGCG GGTTACACAG AATATATAAC
        550        560        570        580        590        600
ATCGTAGGTG TCTGGGTGAA CAGTTTATCC CTGGCATCCA CTAAATATAA TGGAGCTCGC
        610        620        630        640        650        660
TTTTAAGCTG GCATCCAGAA AAAAAAAGAA TCCCAGCACC AAAATATTGT TTTCTTCACC
        670        680        690        700        710        720
AACCATCAGT TCATAGGTCC ATTCTCTTAG CGCAACTACA GAGAACAGGG GCAGAAACAG
        730        740        750        760        770        780
GCAAAAAACG GGCACAACCT CAATGGAGTG ATGCAACCTG CCTGGAGTAA ATGATGACAC
        790        800        810        820        830        840
AAGGCAATTG ACCCACGCAT GTATCTATCT CATTTTCTTA CACCTTCTAT TACCTTCTGC
        850        860        870        880        890        900
TCTCTCTGAT TTGGAAAAAG CTGAAAAAAA AGGTTGAAAC CAGTTCCCTG AAATTATTCC
        910        920        930        940        950        960
CCTACTTGAC TAATAAGTAT ATAAAGACGG TAGGTATTGA TTGTAATTCT GTAAATCTAT
        970        980        990       1000       1010       1020
TTCTTAAACT TCTTAAATTC TACTTTTATA GTTAGTCTTT TTTTTAGTTT TAAAACACCA
       1030       1040       1050       1060
AGAACTTAGT TTCGAATAAA CACACATAAA CAAACAAGCT T
```

FIG.2

```
                -900                                                -850
GATCCAAATGTAAATAAACAATCACAAGGAAAAAAAAAAAAAAAAAAAAAAAATAGCCGCCATG
                                                    -800
ACCCCGGATCGTCGGCTTGTGATACGGTCAGGGTAGCGCCCTGGTCAAAC
                                                    -750
TTCAGAACTAAAAAAATAACTAAGGAAGAAAAAAATAGCTAATTTTTCCG
                                                    -700
GCAGAAAGATTTTCGCTACCCGAAAGTTTTTCCGGCAAGCTAAATGGAAA
                                                    -650
AAGGAAAGATTATTGAAAGAGAAAGAAAGAAAAAAAAAAAAATGTACACCC
                                                    -600
AGACATCGGGCTTCCATAATTTCGGCTCTATTGTTTTCCATCTCTCGCAA
                                                    -550
CGGCGGGATTCCTCTATGGCGTGTGATGTCTGTATCTGTTACTTAATCCA
                                                    -500
GAAACTGGCACTTGACCCAACTCTGCCACGTGGGTCGTTTTGCCATCGAC
                                                    -450
AGATTGGGAGATTTTCATAGTAGAATTCAGCATGATAGCTACGTAAATGT
                                                    -400
GTTCCGCACCGTCACAAAGTGTTTTCTACTGTTCTTTCTTCTTTCGTTCA
                                                    -350
TTCAGTTGAGTTGAGTGAGTGCTTTGTTCAATGGATCTTAGCTAAAATGC
                                                    -300
ATATTTTTCTCTTGGTAAATGAATGCTTGTGATGTCTTCCAAGTGATTT
                                                    -250
CCTTTCCTTCCCATATGATGCTAGGTACCTTTAGTGTCTTCCTAAAAAAA
                                                    -200
AAAAAAGGCTCGCCACTCAAAACGATATTCGTTGGCTTTTTTTTCTGAAT
                                                    -150
TATAAATACTCTTTGGTAACTTTTCATTTCCAAGAACCTCTTTTTTCCAG
                                                    -100
TTATATCATGGTCCCCTTTCAAAGTTATTCTCTACTCTTTTTCATATTCA
                                                    -50
TTCTTTTTCATCCTTTGGTTTTTTATTCTTAACTTGTTTATTATTCTCTC
                     *                              -10
TTGTTTCTATTTACAAGACACCAATCAAAACAAATAAAACATCATCACA
```

FIG. 4-1

```
  1                                                       10                                                      20
met ser arg leu glu arg leu thr ser leu asn val val ala gly ser asp leu arg arg
ATG TCT AGA TTA GAA AGA TTG ACC TCA TTA AAC GTT GTT GCT GGT TCT GAC TTG AGA AGA 30                                                      40
thr ser ile ile gly thr ile gly pro lys thr asn asn pro glu thr leu val ala leu
ACC TCC ATC ATT GGT ACC ATC GGT CCA AAG ACC AAC AAC CCA GAA ACC TTG GTT GCT TTG 50                                                      60
arg lys ala gly leu asn ile val arg met asn phe ser his gly ser tyr glu tyr his
AGA AAG GCT GGT TTG AAC ATT GTC CGT ATG AAC TTC TCT CAC GGT TCT TAC GAA TAC CAC 70                                                      80
lys ser val ile asp asn ala arg lys ser glu glu leu tyr pro gly arg pro leu ala
AAG TCT GTC ATT GAC AAC GCC AGA AAG TCC GAA GAA TTG TAC CCA GGT AGA CCA TTG GCC 90                                                     100
ile ala leu asp thr lys gly pro glu ile arg thr gly thr thr thr asn asp val asp
ATT GCT TTG GAC ACC AAG GGT CCA GAA ATC AGA ACT GGT ACC ACC ACC AAC GAT GTT GAC 110                                                     120
tyr pro ile pro pro asn his glu met ile phe thr thr asp asp lys tyr ala lys ala
TAC CCA ATC CCA CCA AAC CAC GAA ATG ATC TTC ACC ACC GAT GAC AAG TAC GCT AAG GCT 130                                                     140
cys asp asp lys ile met tyr val asp tyr lys asn ile thr lys val ile ser ala gly
TGT GAC GAC AAG ATC ATG TAC GTT GAC TAC AAG AAC ATC ACC AAG GTC ATC TCC GCT GGT 150                                                     160
arg ile ile tyr val asp asp gly val leu ser phe gln val leu glu val val asp asp
AGA ATC ATC TAC GTT GAT GAT GGT GTT TTG TCT TTC CAA GTT TTG GAA GTC GTT GAC GAC 170                                                     180
lys thr leu lys val lys ala leu asn ala gly lys ile cys ser his lys gly val asn
AAG ACT TTG AAG GTC AAG GCT TTG AAC GCC GGT AAG ATC TGT TCC CAC AAG GGT GTC AAC 190                                                     200
leu pro gly thr asp val asp leu pro ala leu ser glu lys asp lys glu asp leu arg
TTA CCA GGT ACC GAT GTC GAT TTG CCA GCT TTG TCT GAA AAG GAC AAG GAA GAT TTG AGA 210                                                     220
phe gly val lys asn gly val his met val phe ala ser phe ile arg thr ala asn asp
TTC GGT GTC AAG AAC GGT GTC CAC ATG GTC TTC GCT TCT TTC ATC AGA ACC GCC AAC GAT 230                                                     240
val leu thr ile arg glu val leu gly glu gln gly lys asp val lys ile ile val lys
GTT TTG ACC ATC AGA GAA GTC TTG GGT GAA CAA GGT AAG GAC GTC AAG ATC ATT GTC AAG 250                                                     260
ile glu asn gln gln gly val asn asn phe asp glu ile leu lys val thr asp gly val
ATT GAA AAC CAA CAA GGT GTT AAC AAC TTC GAC GAA ATC TTG AAG GTC ACT GAC GGT GTT 270                                                     280
met val ala arg gly asp leu gly ile glu ile pro ala pro glu val leu ala val gln
ATG GTT GCC AGA GGT GAC TTG GGT ATT GAA ATC CCA GCC CCA GAA GTC TTG GCT GTC CAA 290                                                     300
lys lys leu ile ala lys ser asn leu ala gly lys pro val ile cys ala thr gln met
AAG AAA TTG ATT GCT AAG TCT AAC TTG GCT GGT AAG CCA GTT ATC TGT GCT ACC CAA ATG 310                                                     320
leu glu ser met thr tyr asn pro arg pro thr arg ala glu val ser asp val gly asn
TTG GAA TCC ATG ACT TAC AAC CCA AGA CCA ACC AGA GCT GAA GTT TCC GAT GTC GGT AAC 330                                                     340
ala ile leu asp gly ala asp cys val met leu ser gly glu thr ala lys gly asn tyr
GCT ATC TTG GAT GGT GCT GAC TGT GTT ATG TTG TCT GGT GAA ACC GCC AAG GGT AAC TAC 350                                                     360
pro ile asn ala val thr thr met ala glu thr ala val ile ala glu gln ala ile ala
CCA ATC AAC GCC GTT ACC ACT ATG GCT GAA ACC GCT GTC ATT GCT GAA CAA GCT ATC GCT
```

FIG. 4-2

```
                                    370                                           380
tyr leu pro asn tyr asp asp met arg asn cys thr pro lys pro thr ser thr thr glu
TAC TTG CCA AAC TAC GAT GAC ATG AGA AAC TGT ACT CCA AAG CCA ACC TCC ACC ACC GAA 390                                    400
thr ser leu pro arg val ala ala val phe glu gln lys ala lys ala ile ile val leu
ACG TCG CTG CCT CGT GTC GCT GCT GTT TTC GAA CAA AAG GCC AAG GCT ATC ATT GTC TTG 410                                           420
ser thr ser gly thr thr pro arg leu val ser lys tyr arg pro asn cys pro ile ile
TCC ACT TCC GGT ACC ACC CCA AGA TTG GTT TCC AAG TAC AGA CCA AAC TGT CCA ATC ATC 430                                    440
leu val thr arg cys pro arg ala ala arg phe ser his leu tyr arg gly val phe pro
TTG GTT ACC AGA TGC CCA AGA GCT GCT AGA TTC TCT CAC TTG TAC AGA GGT GTC TTC CCA 450                                           460
phe val phe glu lys glu pro val ser asp trp thr asp asp val glu ala arg ile asn
TTC GTT TTC GAA AAG GAA CCT GTC TCT GAC TGG ACT GAT GAT GTT GAA GCC CGT ATC AAC 470                                    480
phe gly ile glu lys ala lys glu phe gly ile leu lys lys gly asp thr tyr val ser
TTC GGT ATT GAA AAG GCT AAG GAA TTC GGT ATC TTG AAG AAG GGT GAC ACT TAC GTT TCC 490                               499
ile gln gly phe lys ala gly ala gly his ser asn thr leu gln val ser thr val OC
ATC CAA GGT TTC AAG GCC GGT GCT GGT CAC TCC AAC ACT TTG CAA GTC TCT ACC GTT TAA +10                                                +50
AAAAAGAATCATGATTGAATGAAGATATTATTTTTTTGAATTATATTTTT

*****     +100
TAAATTTTATATAAAGACATGGTTTTTCTTTTCAACTCAAATAAAGATTT

*****                                              +150
ATAAGTTACTTAAATAACATACATTTTATAAGGTATTCTATAAAAAGATA

+200
ACTTATGTTATTGTTAACCTTTTTGTCTCCAATTGTCGTCATAACGATGA

+250
GGTGTTCGATTTTTGGAAACGAGATTGACATAGAGTCAAAATTTGCTAAA

+300
TTTGATCCCTCCCATCGCAAGATAATCTTCCCTCAAGGTTATCATGATTA

*****            +350
TCAGGATGGCGAAAGGATACGCTAAAAATTCAATAAAAAATTCAATATAA

+400
TTTTCGTTTCCCAAGAACTAACTTGGAAGGTTATACATGGGTACATAAAT

+450
GCAGATGCCAGTGAACTATGTTCAGCTTCTGGCCTTCGTTTGGTGGTTTA

ATCTATTTTTTATAAAAAATGACG
```

FIG.4-3

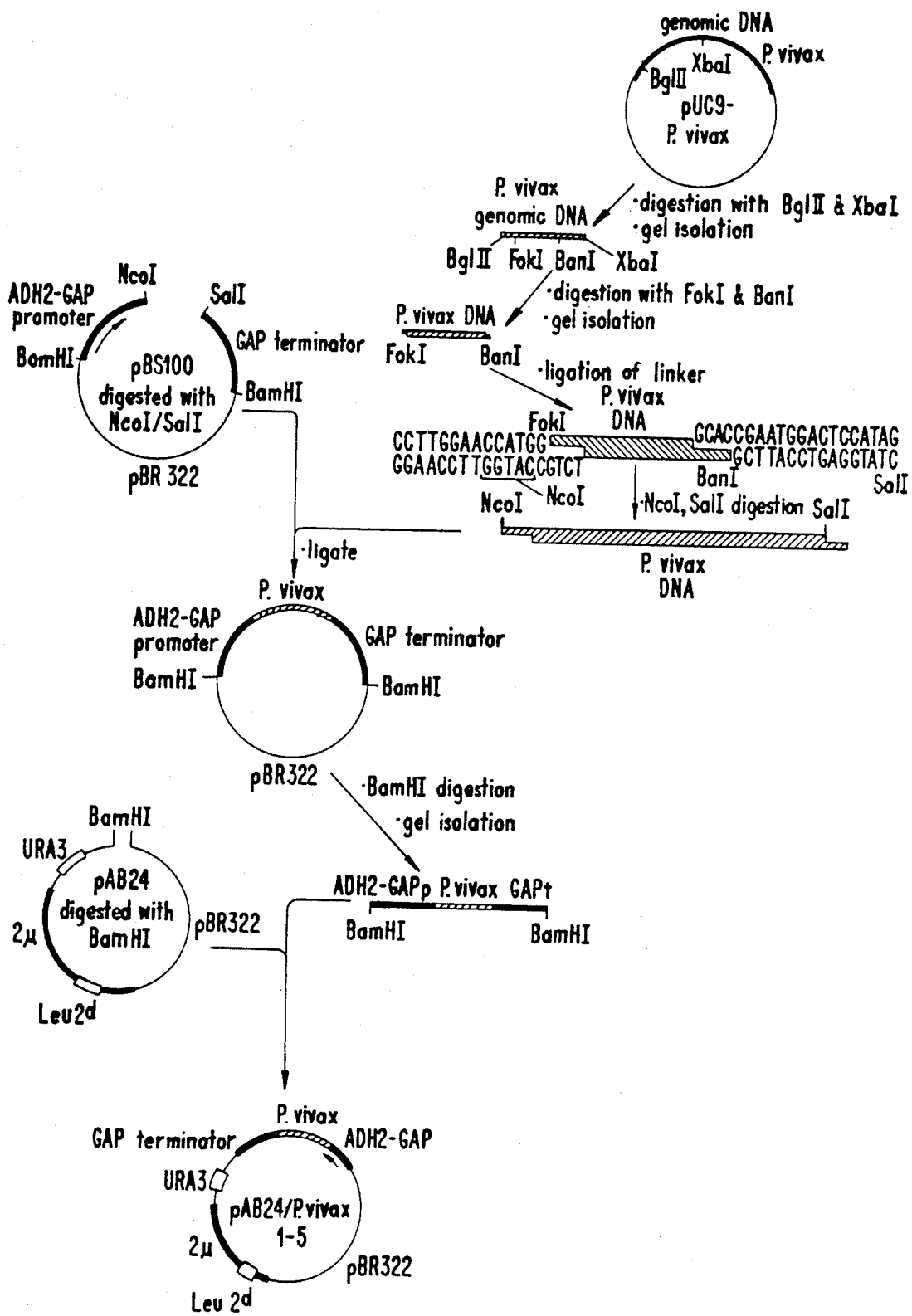
CONSTRUCTION OF A YEAST EXPRESSION PLASMID FOR P. vivax DNA
FIG._9a.

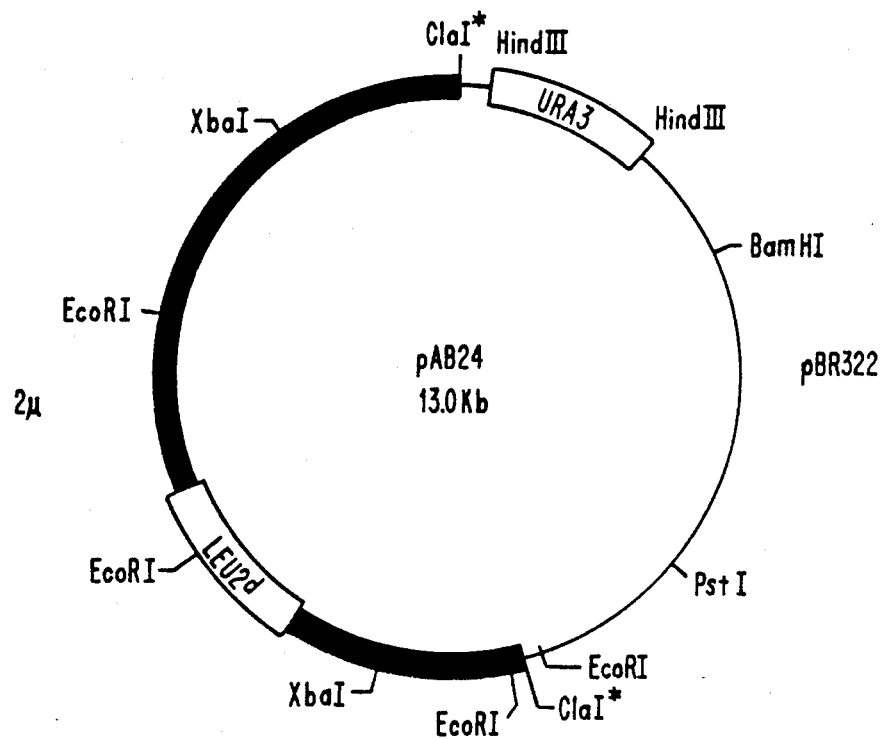
YEAST EXPRESSION PLASMID pAB24
FIG._9b.

EUKARYOTIC REGULATABLE TRANSCRIPTION

CROSS-REFERENCE TO RELATED APPLICATIONS

This is a continuation-in-part of U.S. application Ser. No. 760,197 filed July 29, 1985, which is a continuation-in-part of U.S. application Ser. No. 468,589 filed Feb. 22, 1983, now abandoned, and U.S. application Ser. No. 609,540 filed May 11, 1984, now abandoned, which disclosures are incorporated herein by reference.

BACKGROUND OF THE INVENTION

1. Field of the Invention

The advent of hybrid DNA technology provided a unique opportunity to produce peptides of any sequence of naturally-occurring amino acids. Thus, for the first time, macromolecules could be prepared at will from a large number of different monomers to provide a specifically defined sequence. Once the feasibility had been established, there was then an interest in the economics of the technology, in providing systems which could be adapted to the production of particular products.

In part, because of the familiarity with *E. coli*, *E. coli* was an obvious host for research expression and potentially for commercial expression of products of interest. However, *E. coli*, as well as other prokaryotes, have a number of disadvantages. Many of the prokaryotes produce endo- or exotoxins. Therefore, the resulting product must be carefully purified to ensure the absence of any materials which would affect the health of the patient. This can be particularly troublesome, where the product is administered chronically.

Yeast as a host does not suffer from many of the disadvantages of prokaryotes and, furthermore, has a number of advantages. Yeast has been used for a long time in fermentation, so that there are a number of commercial hosts which have a number of desirable properties, such as resistance to viral infection, rapid growth, stability, and the like. In addition, yeast can provide in certain situations glycosylation of the product, so as to provide a peptide product which has a verisimilitude to the naturally-occurring glycosylated product.

In order to use yeast as a host, it will be necessary to provide a number of different constructs which allow for expression under a variety of conditions. In many situations, one may wish to have controlled expression, where a change in the nutrient medium may actuate or inhibit expression. Furthermore, since yeast secretes a number of different products naturally, the secretion mechanism may be available for secretion of a variety of peptides foreign to yeast. Thus, yeast provide an attractive opportunity for the development of economical and efficient production of peptides.

2. Description of the Prior Art

Krebs, *J. Biol. Chem.* (1953) 200: 471 and Maitra and Lobo, ibid. (1971) 246: 475 describe properties of glyceraldehyde-3-phosphate dehydrogenate (GAPDH) in yeast. Cloning of GAPDH genes or the pyruvate kinase (PyK) gene has been described by Holland, et al., *Basic Life Science* (1981) 19: 291; and Kawasaki and Fraenkel, *Biochem. Biophys. Res. Comm.* (1982) 108: 1107. Yeast promoters which have been linked to foreign genes include alcohol dehydrogenase I (ADHI) (Valenzuela, et al., *Nature* (1982) 298: 347; Hitzeman, et al., ibid. (1981) 293: 717) and phosphoglycerate kinase (Tuite, et al., *EMBO* (1980) 1: 603; Hitzeman, et al., *Science* (1983) 219: 620). Beier and Young, *Nature* (1982) 300: 724 reports the use of ADR3 as a regulatory sequence. GB 2,154,240 published Sept. 4, 1985, describes the immunodominant epitope of the circumsporozoite protein. See also, Nussenzweig and Nussenzweig, *Cell* (1985) 42: 401–403 and Arnot et al., *Science* (1985) 230: 815–817, which describe the gene for the immunodominant protein.

SUMMARY OF THE INVENTION

Novel DNA constructs are provided including a transcription control region comprising a first transcriptional regulatory region and a second transcriptional initiation region, where the two regions may be derived from different sources. Particularly, the transcriptional initiation regions are associated with yeast glycolytic enzymes, while the transcriptional regulatory regions may or may not be derived from regions associated with yeast glycolytic enzymes. The transcriptional control region (the regulatory region and initiation region) is joined to a gene not naturally associated with the transcriptional control region. A terminator region is also present linked to the foreign gene to assure transcription termination. In conjunction, these elements provide for an expression construct ("expression cassette") which can be introduced into a yeast host for maintenance as an extrachromosomal element or integration into the yeast genome. Optionally, a secretory leader can be provided which allows for secretion of the desired peptide product or for targeting of the product onto the secretion pathway.

BRIEF DESCRIPTION OF THE DRAWINGS

FIG. 2: DNA sequence of the GAPDH promoter fragment;

FIG. 4: Nucleotide sequence of the pyruvate kinase (PyK) gene;

FIG. 9a provides a flow diagram for preparation of a yeast expression plasmid for expressing *P. vivax* circumsporozoite protein, while FIG. 9b is a diagrammatic view of plasmid pAB24.

DESCRIPTION OF THE SPECIFIC EMBODIMENTS

Figure 1:
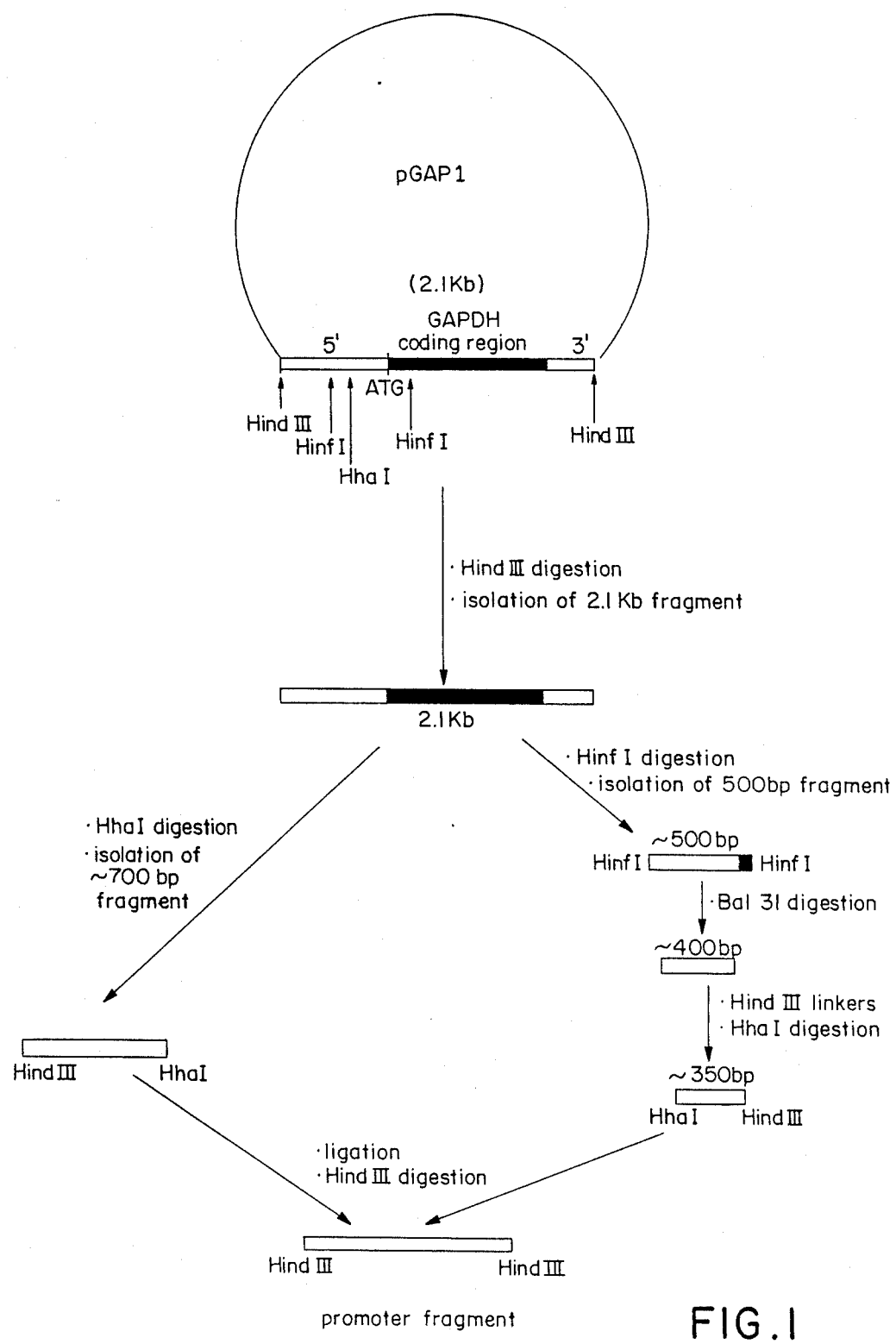
FIG. 1: Isolation and tailoring of a GAPDH promoter fragment.

Yeast systems are provided for the efficient, economical expression of peptides. Transcriptional control regions are provided having first and second regions, a first transcriptional regulatory region which provides for constitutive or inducible transcription and a second transcription initiation region to provide for efficient transcription of a structural gene. Optionally, downstream from the transcriptional initiation region, a sequence coding for a leader peptide and processing signal can be provided, so that a propeptide is expressed comprising the secretory leader sequence, processing signal and expression product of the foreign heterologous gene, which may be secreted and processed to provide for a mature peptide. Various constructs are devised to allow for high levels of expression in economic and efficient manners.

The transcriptional control region (previously referred to as the "promoter region" in application Ser. No. 609,540) will have two domains: (1) the structural gene proximal region, the transcriptional initiation region, will include the transcription initiation site, the "TATA" sequence, capping sequence as appropriate, and an RNA polymerase binding sequence, which sequence intends a sequence which includes nucleotides upstream from the initiation site for directing the initiation of synthesis of the messenger RNA; and (2) a structural gene distal region, or upstream activator sequence (UAS) which provides for regulated or constitutive expression, which may be naturally associated with the transcriptional initiation region or an unnatural association, resulting from manipulative involvement of the sequences, so as to produce a transcriptional control region which is not naturally found. This regulation may be of a positive or negative manner resulting in the enhancement or remission of transcription.

The hybrid or chimeric transcriptional control regions provide for enhanced efficiencies of transformation and greatly improve viability of the yeast host as contrasted with those employing a wild-type yeast promoter in those cases where expression of the foreign gene is deleterious. Concomitant with the improved viability is increased expression of a foreign heterologous gene, in comparison with the truncated transcriptional control region lacking the transcriptional regulatory region, or the naturally-occurring transcriptional control region, and, therefore, greatly enhanced overall yields of expression products are obtained.

The transcriptional control regions of the subject invention employ the transcriptional initiation region of a yeast glycolytic enzyme promoter and a region upstream from said transcriptional initiation region, which may be the same or different from the wild-type upstream region of the transcriptional initiation region and provides for enhanced efficiencies of transcription. This distal region will be derived from either a sequence, usually a yeast sequence, involved in regulation of transcription, or a prokaryotic sequence which provides for enhanced constitutive expression of the desired gene.

Conveniently, cassettes or constructs can be prepared which provide for one or more restriction sites intermediate to the transcriptional control region and a related terminator region where the structural gene may be inserted, so as to be under the transcriptional control of the transcriptional control region. By having one or more restriction sites, one can provide for ease of insertion of the structural gene intermediate to the transcription initiation and termination regions. The cassettes which can be prepared comprising the transcriptional initiation and termination region, having appropriate restriction sites for structural gene insertion can be cloned in prokaryotic vectors, so that after insertion of the structural gene, the resulting cassette, including the structural gene, may be cloned, isolated and purified, before introduction into a yeast vector.

The cassette, will for the most part, have the following formula:

-(P.R.(2)-P.R.(1))-R.S.-T.R.- wherein:

P.R.(1) is the transcriptional initiation region proximal to the structural gene and having the transcription initiation site, the RNA polymerase binding site, and including when naturally present or as appropriate the TATA box, the CAAT sequence, as well as translational regulatory signals, e.g., capping sequence;

P.R.(2) is the transcriptional regulatory region joined to the 5'-end of P.R.(1), which may be wild-type DNA, yeast DNA other than the DNA normally present in the yeast host, or DNA associated with regulating and/or enhancing the efficiency of transcription of the RNA polymerase binding sequence;

R.S. is a sequence having one or more restriction enzyme recognition sites, preferably at least two restriction enzyme recognition sites, where the sites may result upon restriction in blunt ends or overhangs;

T.R. intends the termination region, which will include the terminator, which may be a stem and loop structure, and which may be associated with one or more stop codons, a polyadenylation signal sequence, if any, as well as any other transcriptional and translational termination sequences.

P.R.(1) will generally be at least about 150 bp, more usually at least about 200 bp, usually not more than about 600 bp, more usually not more than about 500 bp, generally not more than about 450 bp and preferably less than about 400 bp; the sequence will extend in the downstream direction of transcription to bp +25, conveniently about bp +3, more usually bp −1 and may extend only to bp −20, more usually to bp −10 (the numbering intends that +1 is the first bp of the initiation codon with which the transcriptional initiation region is associated in the wild-type host, while −1 is the immediately upstream bp and the integers increase in the direction of transcription;

P.R.(1) will be derived from a strong yeast promoter, normally a glycolytic enzyme promoter, such as glyceraldehyde-3-phosphate dehydrogenase, pyruvate kinase, alcohol dehydrogenase, phosphoglucoisomerase, triose phosphate isomerase, phosphofructokinase, etc.; however, when P.R.(2) is the naturally occurring region P.R.(1) will be derived from glyceraldehyde-3-phosphate dehydrogenase or pyruvate kinase;

P.R.(2) will be the naturally occurring or wild-type upstream region or a transcriptional regulatory region chosen to provide a transcription enhancing and/or regulatory function, which enhancing function may provide for constitutive or regulated transcription; regulators will be derived from regions associated with regulation of yeast genes, other than the natural or wild-type gene associated with the first domain in the wild-type or natural host, such as UDP-galactose epimerase (GAL10), galactokinase (GAL1), acid phosphatase (PHO5), alcohol dehydrogenase I and II, etc. For yeast transcriptional regulatory regions, the domain will usually be at least about 100 bp, more usually at least about 200 bp, for convenience generally not exceeding about 3 kbp, usually not exceeding about 1 kbp, desirably not exceeding about 600 bp. The regulatory region will generally begin at least about 200 bp from the initiation codon, usually at least about 300 bp and may begin at 400 bp or farther upstream from the initiation codon.

Regulation can be as a result of a change in the chemical or physical environment of the host, such as a change in carbon source, e.g., glucose to galactose or vice versa; a change in concentration of a nutrient, e.g., an organic nutrient such as glucose or an inorganic nutrient such as a phosphate; or a change in temperature, e.g., 25° C. to 35° C. Constitutive transcription can be achieved employing prokaryotic sequences of at least about 500 bp, usually 1 kbp or more, for convenience, generally not exceeding about 5 kbp; conveniently, the prokaryotic sequence can be obtained from the vector in which the cassette is cloned, illustrative vectors including pBR322, lambda, Charon 4A, pACYC184, pUC9, etc.

R.S. will generally be at least 4 bp, more usually at least 6 bp, and may be 100 bp or more, more usually being not more than about 60 bp and may include one or more, usually not more than about 10 restriction sites, where such restriction sites may be illustrated by EcoRI, BamHI, SalI, HindIII, AluI, AvaI, TaqI, HpaI, etc., having at least one unique restriction site for the construct sequences.

T.R. is the termination region which will include the necessary transcriptional and translational signals for termination, such as the polyadenylation site, etc.; T.R. will generally be at least about 100 bp, more usually at least 150 bp, and generally less than about 1 kbp, usually less than about 600 kbp; the termination region may be derived from any convenient yeast sequence, so long as the terminator balances the transcriptional initiation region, conveniently being derived from a glycolytic enzyme terminator, where the terminator may be associated with the same or different enzyme with which the transcriptional initiation region is associated.

Where a cassette is cloned in a bacterial vector, the construction will have the following formula:

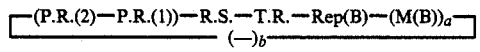

wherein all the symbols have been defined previously, except for:

Rep (B), which intends a replicon or replication sequences recognized and utilized by a prokaryotic host and may be derived from a plasmid or phage, such as ColE1, R plasmid, e.g., pRK290, lambda, e.g., Charon 4A, λdv, etc.;

M is a marker which provides for selection of hosts containing the construction, where (B) intends a prokaryotic, e.g., bacterial, host and a intends an integer of from 0 to 3, usually 1 to 2, although additional markers may be present, where the marker allows for selection of the host containing the construct as well as providing for selective pressure on maintaining hosts having the construct; the markers include biocide resistance, such as antibiotic resistance, toxin resistance and heavy metal resistance; complementation providing prototrophy to an auxotrophic host; providing immunity; and the like;

the markers may provide for complementation of an auxotrophic host, e.g., his$^-$, ura$^-$, trp$^-$, leu$^-$ phenotype, resulting in prototrophy; resistance to metals, such as cup$^+$ genotype; resistance to antibiotics, such as amp$^r$, tc$^r$, cam$^r$, str$^r$, tun$^r$ genotype, etc.;

b is 0 or 1, intending that the construction is either linear or circular, usually circular.

The above construct can be used for insertion of a wide variety of structural genes, both prokaryotic and eukaryotic, both naturally occurring and synthetic, where the genes may include signal leaders for secretion, and the like.

In many situations it will be desirable to provide for secretion of the peptide product or targeting of the product to an appropriate subcellular organelle. This is achieved by employing a sequence coding for a secretory leader sequence and processing signal functional in yeast where the structural gene is joined downstream and in reading frame with the leader and processing signal. Of interest are the wild-type or modified secretory leader and processing signals described in E.P.A. 0 116 201, published Aug. 22, 1984 (α-factor) and E.P.A. 0 123 289, published Oct. 31, 1984. See also E.P.A. 0 123 544, published Oct. 31, 1984 and E.P.A. 0 123 297, published Oct. 31, 1984.

Of particular interest is the leader sequence of α-factor which is described in Kurjan and Herskowitz, Abstracts of Papers presented at the 1981 Cold Spring Harbor Meeting on the Molecular Biology of Yeasts, page 242, mutants thereof, where there may be up to five differences in the leader sequence involving up to five base pairs, the differences including transitions, transversions, insertions, deletions, inversions, and the like.

Where one is using α-factor for secretion and processing, it would be appropriate to provide for enhanced expression of the gene STE13, the enzyme dipeptidyl amino peptidase A. Enhanced production can be achieved by providing an increased number of copies of the gene with appropriate sequences for expression or providing a construct having a transcriptional control region resulting in enhanced expression of the enzyme.

The genes employed in the subject constructs may express enzymes, e.g. superoxide dismutase; blood factors, e.g. Factor VIIIc; hormones, e.g. interleukin-II, epidermal growth factor α- and β-transforming growth factor, platelet derived growth factor, cachexin, skeletal growth factor, etc.; proteins from pathogens for vaccines, e.g. viruses such as hepatitis A and B viruses, etc; and such organisms as Plasmodia; structural proteins; lymphokines, membrane surface proteins, immunoglobulins; blood proteins; enzyme regulators, e.g. α'-antitrypsin; mutants thereof, or the like. The particular structural gene which is inserted is not critical to this invention and any polypeptide or protein of interest may be prepared employing the constructions of the subject invention. The structural genes will usually be an unnatural gene (not naturally associated with the transcriptional initiation region) more usually foreign to the yeast host, where foreign intends different from wild-type yeast structural genes and from a source that does not normally exchange genetic information with yeast. The structural genes may encode substantially the entire polypeptide, physiologically active mutants thereof, or immunologically active fragments thereof.

Usually, the structural gene will be at least about 36 bp, and not more than about 20 kbp, usually not more than about 3000 bp, usually not more than about 1500 bp. Included with the structural gene may be noncoding flanking regions, the 5'-flanking region normally being quite short, usually less than about 30 bp, while the 3'-flanking region may be extended, usually not exceeding about 500 bp. Thus, the structural gene fragment will usually include the translational stop codons for proper termination of amino acid chain extension. The structural gene may include introns having appropriate donor and acceptor splicing sites, but will usually be intron free. Therefore, mammalian introns containing genes will frequently involve cDNA.

When the structural gene has been inserted into the cassette which is joined to a yeast replication system, normally including one or more markers recognized by yeast, the resulting construct will have the following formula:

$$\boxed{-(P.R.(2)-P.R.(1))-\text{gene}-T.R.-\text{Rep}(Y)-(M(Y))_a\phantom{-}}$$

wherein all of the symbols have been defined previously except for:
gene, which intends the structural gene, having its initiation codon and stop codons as appropriate; and
Y, which intends that the symbol is related to yeast.

Convenient yeast replication systems include the 2μ plasmid replication system, combination of CEN3 and ARS1 or ARS3, or the like. The replication systems may be high or low copy number, depending on the effect of the construct on the viability of the host. While the indicated replication system are those which have found common employment, any replication system useful in yeast may be employed which provides for efficient replication and maintenance. Often the structural gene will be inserted into an appropriate shuttle vector capable of replication and selection in either a yeast or bacterial host, (a shuttle vector) where the resulting construction will have the following formula:

$$\boxed{-(P.R.(2)-P.R.(1))-\text{gene}-T.R.-\text{Rep}(Y)-(M(Y))_a-\text{Rep}(B)-(M(B))_a\phantom{-}}$$

where all symbols have been defined previously. Also, it is, of course, understood that the cassette without an inserted structural gene but containing the restriction enzyme recognition sequence, R.S., may be propagated in yeast or contained within a shuttle vector, where the construction will have the following respective formulae:

$$\boxed{-(P.R.(2)-P.R.(1))-R.S.-T.R.-\text{Rep}(Y)-(M(Y))_a\phantom{-}}$$

$$\boxed{-(P.R.(2)-P.R.(1))-R.S.-T.R.-\text{Rep}(Y)-(M(Y))_a-\text{Rep}(B)-(M(B))_a\phantom{-}}$$

where all symbols have been defined previously.

Where integration of the construct is desired DNA homologous with the yeast host chromosomal DNA may be included with the construct, particularly where the DNA may complement auxotrophy. In this situation, a replication system providing for stable episomal maintenance is not required.

The various fragments which form the cassette and final constructions may be joined together in accordance with conventional ways. In many cases, genes have been isolated and restriction mapped, as well as sequenced. To that extent, one can select the sequence of interest by restriction of the gene, employing further manipulation as necessary such as resection with Bal31, in vitro mutagenesis, primer repair, or the like, to provide a fragment of a desired size, including the desired sequence, and having the appropriate termini. Linkers and adapters can be used for joining sequences, as well as replacing lost sequences, where the restriction site is internal to the region of interest. The various fragments which are isolated, may be purified by electrophoresis, electroeluted, ligated to other sequences, cloned, reisolated and further manipulated.

The use of regulatory sequences for controlling transcription of the structural gene of interest allows for growing the host cells to high density with no or low levels of expression of the structural gene, and then inducing expression by changing the environmental conditions, e.g., nutrient, temperature, etc.

For example, with the GAL4 regluatory region, the yeast cells could be grown in rich media with a glycerol-lactic acid combination to high density, e.g., mid or late log phase, followed by switching the carbon source to galactose. For PHO5 regulation one could grow the cells at high phosphate, about 1 to 10 mM and then decrease the phosphate concentration to about 0.1 to 0.5 mM. For temperature sensitivity, one could grow the cells at 25° to 37° C. and then change the temperature as appropriate by about 5° C. The host cells would have the regulatory system associated with the regulatory regimen employed.

For ADH2, the transcriptional regulatory region is derepressed in the absence of a readily available source of glucose (without exogenous inducer). The transcriptional regulatory region is found to be functional in a wide variety of Saccharomyces strains. By allowing for glucose exhaustion after the yeast culture is grown to high density, the transcriptional control region will be derepressed and expression of the desired peptide will occur.

Various techniques will be exemplified in the Experimental section of this application, which techniques can be used as paradigmatic for constructions employing fragments from sources other than those exemplified. Of particular interest, as evidenced by the Experimental section, will be the use of the glyceraldehyde-3-phosphate dehydrogenase promoter region for the RNA polymerase binding site in conjunction with regulator sequences, such as those associated with GAL1-10 (GAL4), PHO5, ADH2 (ADR3), or the like. In referring to the GAL4 regulatory region or associated sequence, the region intends the sequence associated with regulation of other galactose metabolism genes, e.g., GAL1 and GAL10, which are under the regulatory control of such sequence in conjuction with the expression product of the GAL4 gene. The PHO5 and ADH2 sequences refer to regions associated with the PHO5 and ADH2 genes which provide for transcriptional regulation of the PHO5 and ADH2 genes.

The following examples are offered by way of illustration and not by way of limitation.

EXPERIMENTAL

All DNA manipulations were done according to standard procedures. See *Molecular Cloning*, T. Maniatis et al., Cold Spring Harbor Lab., 1982. Enzymes used in cloning were utilized as per the manufacturer's specifications. Enzymes were obtained either from New England Biolabs or Bethesda Research Laboratories. Procedures with these enzymes employed the supplier's directions. Yeast were transformed and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. In the case of plating medium contained 2% (w/v) agar and for transformation 3% top agar with 1M sorbitol. Hepatitis B surface antigen was determined after lysis of yeast by glass bead agitation and clarification by centrifugation, using the AusriaII assay (Abbott Laboratories). Protein is determined by the Coomassie dye binding method.

E. coli strains useful for transformation include X1776; K12 strain 294 (ATCC No. 31446); RR1, HB101 and D1210. Yeast strains XV610-8c (a ade2 ade6 leu2 lys1 trp1 can1), GM-3C-2 (leu2 trp1 his4 CYC1-1 CYP3-1) (Faye, G. et. al., Proc. Natl. Acad. Sci. (1981) 78:2258), S. cerevisiae AB103.1 (Mata, pep4-3, leu2-3, leu2-112, ura3-52, his4-580, cir°) and S. cerevisiae AB110 (Mata, ura3-52, leu2-04, or both leu2-3 and leu2-112, pep4-3, his4-580, cir°), can be typically used for yeast transformations. It would be understood, however, that virtually any strain of yeast is useful for transformation. Bacteria can be grown and selected according to procedures described by Miller, J. H., *Experiments in Molecular Genetics,* Cold Spring Harbor Laboratory, Cold Spring Harbor, N.Y. (1972). Yeast can be grown on the following media: YNB plus CAA contains 6.7 grams of yeast nitrogen base (Difco Laboratories, Minneapolis, Minn.), 10 mg of adenine, 10 mg of uracil, 5 g casamino acids (CAA) (Difco), 20 g glucose; and, in the cse of plating media, 30 g agar per liter. Selection for tryptophan prototrophy can be made on plates containing 6.7 g yeast nitrogen base (lacking amino acids), supplemented for all growth requirements of the strain to be transformed except tryptophan.

EXAMPLE 1

Cloning of the yeast glyceraldehyde-3-phosphate dehydrogenase (GAPDH) gene

A complementary DNA (cDNA) containing the yeast GAPDH coding sequences was prepared in the following manner:

PolyA+ RNA was isolated from yeast strain A364A. Double-stranded cDNA was synthesized using AMV reverse transcriptase and E. coli DNA polymerase I. Poly-dC-tails were added to the double-stranded cDNA molecule using deoxynucleotide terminal transferase. Poly-dC-tailed cDNA was annealed to poly-dG-tailed pBR322 and used to transform E. coli HB101. One thousand transformants were screened by colony hybridization to labeled PolyA+ RNA, and a subset further examined by restriction endonuclease mapping, and DNA sequencing. Three clones containing GAPDH sequences were isolated from the pool. One clone (pcGAP-9) contained an insert of about 1200 base pairs (bp) and was used for further work.

A yeast gene library was prepared by inserting fragments obtained after partial digestion of total yeast DNA with restriction endonuclease Sau3A into lambda phage Charon 28, according to Blattner, F. R. et al., *Science* (1977) 196:161-169. Several fragments containing yeast GAPDH coding sequences were isolated by screening the phage library with labeled DNA from pcGAP-9. The yeast GAPDH gene of one of these clones was subcloned in pBR322 as a 2.1 kb HindIII fragment (pGAP-1, see FIG. 1) or as a 3.5 kb BamHI fragment (pGAP-2). The GAPDH promoting-active fragments were isolated from these clones. The HindIII-HhaI fragment of about 700 bp was ligated to the HhaI-HindIII fragment of about 350 bp and subsequently digested with HindIII (see FIG. 1). The resulting HindIII (about 1050 bp) fragment was isolated by gel electrophoresis and cloned in pBR322, (pGAP-347), and the sequence determined (see FIG. 2).

EXAMPLE 2

Figure 3:
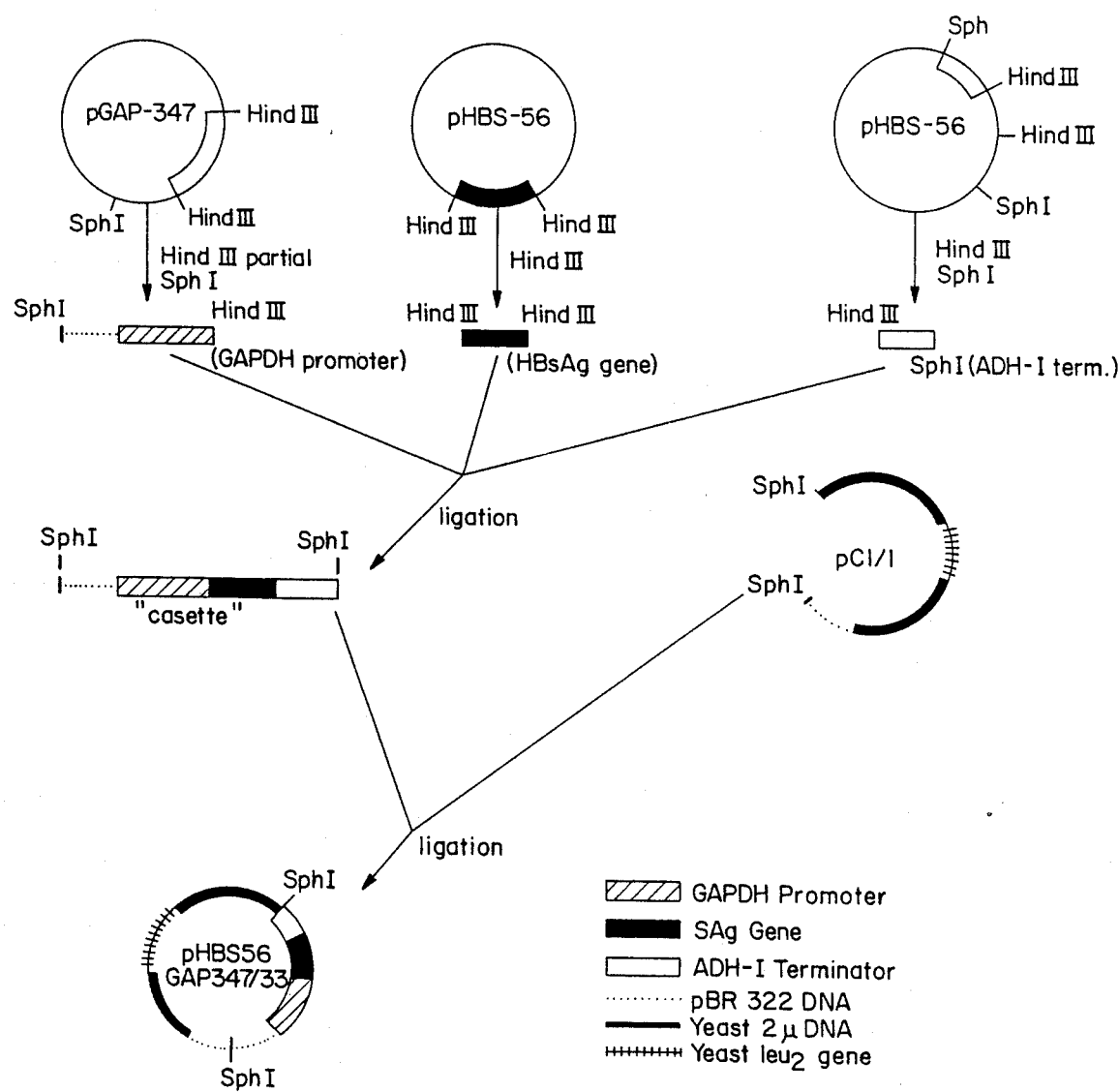
FIG. 3: Construction of a yeast expression plasmid containing the GAPDH promoter.

Construction of yeast vectors containing the GAPDH promoter, active in the expression of HBsAg A plasmid vector (pHBS56-GAP347/33, ATCC Accession No. 20665), for the expression of HBV surface antigen in yeast, using the GAPDH promoter fragment was constructed as depicted in FIG. 3.

Total digestion of pGAP-347 with SphI followed by partial digestion with HindIII yielded an approximtely 1700 bp SphI-HindIII fragment having about 1060 bp of GAPDH promoter and about 530 bp of pBR322. The 1700 bp SphI-HindIII GAPDH promoter fragment was ligated with the 840 bp HindIII-HindIII fragment (containing the HBsAg coding region, 26 bases of 5' 1 non-coding region and 128 bp of 3' non-coding region, obtained from pHBS56) and then with the 350 bp HindIII-SphI fragment containing the ADH-1 termination region (isolated from pHBS56). The 2900 bp SphI fragment (cassette) was isolated and cloned in pHBS56 previously digested with SphI. The plasmid pHBS56 (ATCC Accession No. 40047) has been described in a co-pending application (Ser. No. 402,330, filed July, 27, 1982, titled "Synthesis of Human Virus Antigens by Yeast", herein incorporated by reference) and contains the entire 2μ plasmid, a region with the yeast leu2 gene, the amp resistance locus of pBR322 and the sAg gene under regulation of the ADH promoter and terminator (described in Example 8). The resulting plasmid (pHBS56-GAP347/33) in which the promoter, gene and termination regions were in the proper orientations was isolated and used to transform yeast strain AB102 (MATa, pep 4-3, leu 2-3 leu2-112, ura 3-52, his 4-580, cir°) or strain 2150-2-3 (MATa, ade1, leu2-04, cir°). Strain AB102 is derived from SF657-9c by curing of 2 micron plasmids. Strain 2150-2-3 is from the collection of Dr. Leland Hartwell at the University of Washington.

EXAMPLE 3

Synthesis of HBsAg in yeast under GAPDH promoter control (plasmid pHBS56-GAP347/33)

One hundred ml cultures of strain AB102 containing plasmid pHBS56-347/33 were grown to optical density at 650 nm of 1. Cell-free lysates were prepared by agitation with glass beads and removal of cell debris by centrifugation. HBsAg was measured by the Abbott AusriaII radioimmunoassay and protein concentration was determined by the Coomassie blue binding method. The results are shown in Table 1. They indicate that the GAPDH promoter is about 5 times more effective than the ADH-1 promoter for protein product expression in yeast.

TABLE 1

| | Synthesis of HBsAg in yeast | | |
|---|---|---|---|
| Exp # | sAg (μg/ml) | protein (mg/ml) | Spec. Activity (μgsAg/mg protein) |
| | (a) control from pHBS56 (ADH-I promoter) | | |
| 1 | 8.8 | 18 | 0.49 |
| 2 | 14 | 25 | 0.56 |
| 3 | 12.4 | 20 | 0.62 |

TABLE 1-continued

Synthesis of HBsAg in yeast

| Exp # | sAg (μg/ml) | protein (mg/ml) | Spec. Activity (μgsAg/mg protein) |
|---|---|---|---|
| (b) from pHBS56-GAP347/33 (GAPDH promoter) | | | |
| 1 | 36 | 14 | 2.6 |
| 2 | 35 | 12 | 2.9 |
| 3 | 37 | 12.5 | 3.0 |

Similar results were obtained by substituting yeast strain 2150-2-3 for yeast strain AB102 and repeating Example 3.

EXAMPLE 4

Cloning of the yeast pyruvate kinase gene

The pyruvate kinase gene was cloned by complementation. A yeast pyruvate kinase minus mutant was transformed with a pool of recombinant YEp24 plasmids containing wild type yeast genomic DNA. The yeast strains S288C (genotype: SUC2, mal, gal2, CUP1) and pyk 1-5 (genotype: a, ade1, leu1, met14, ura3, pyk1-5) were obtained from the Yeast Genetic Stock Center, Department of Biophysics, University of California, Berkeley. The yeast genomic bank used consists of a partial Sau3A digest of total DNA from the strain S288C cloned into the BamHI site of the "shuttle" vector YEp24. The vector YEp24 contains pBR322 sequences for selection and growth in bacteria, the yeast URA3 gene for selection in yeast and an EcoRI fragment of the yeast 2μ circle to ensure plasmid replication and segregation in yeast. The pool includes sufficient independent recombinant plasmids to represent the entire yeast genome.

The strain pyk1-5 is unable to grow on medium containing glucose or lacking uracil because of mutations in this strain at the PyK1 and URA3 loci, respectively. Transformation of this strain with the YEp24 genomic library and selection for transformants which are able to grow on medium lacking uracil and containing glucose selects for those cells which have acquired YEp24 containing the pyruvate kinase gene. Transformation of $3.5 \times 10^8$ pyk1-5 yeast cells with 10 μg of YEp24 recombinant plasmid pool DNA yielded 5 independent transformants which grew in the absence of uracil and the presence of glucose.

Characterization of the insert DNA of these transformants by restriction enzyme analysis indicated that they contained overlapping DNA inserts. We focused on a single transformant, pPyK 9.1, which contained a 7.0 kb insert. The pyruvate kinase gene was localized within this insert by determining which insert-specific restriction fragments hybridized to a mRNA of about 1.7 kb expected for the pyruvate kinase mRNA. The localization of the PyK gene was confirmed by subcloning appropriate regions of the insert DNA and observing complementation of function in the pyk1-5 mutant. A subclone pPyK 9.1.1 which contained the PyK gene on a 4.4 kb insert was sequenced and used in expression plasmid constructions.

EXAMPLE 5

Sequence of the yeast pyruvate kinase gene

A total of 2885 nucleotides of the PyK gene have been sequenced including 1497 nucleotides in a single open reading frame, 911 nucleotides of 5' untranslated region and 477 nucleotides of 3' untranslated region (see FIG. 4). The gene encodes a polypeptide of 499 amino acids to give a monomer molecular weight of 54,608 daltons which agrees well with the expected value for yeast PyK. The amino acid composition derived from the nucleotide sequence also corresponds closely with that measured from the isolated yeast protein. The nucleotide sequence predicts a carboxy terminal value which has been found for yeast pyruvate kinase.

EXAMPLE 6

Figure 5:
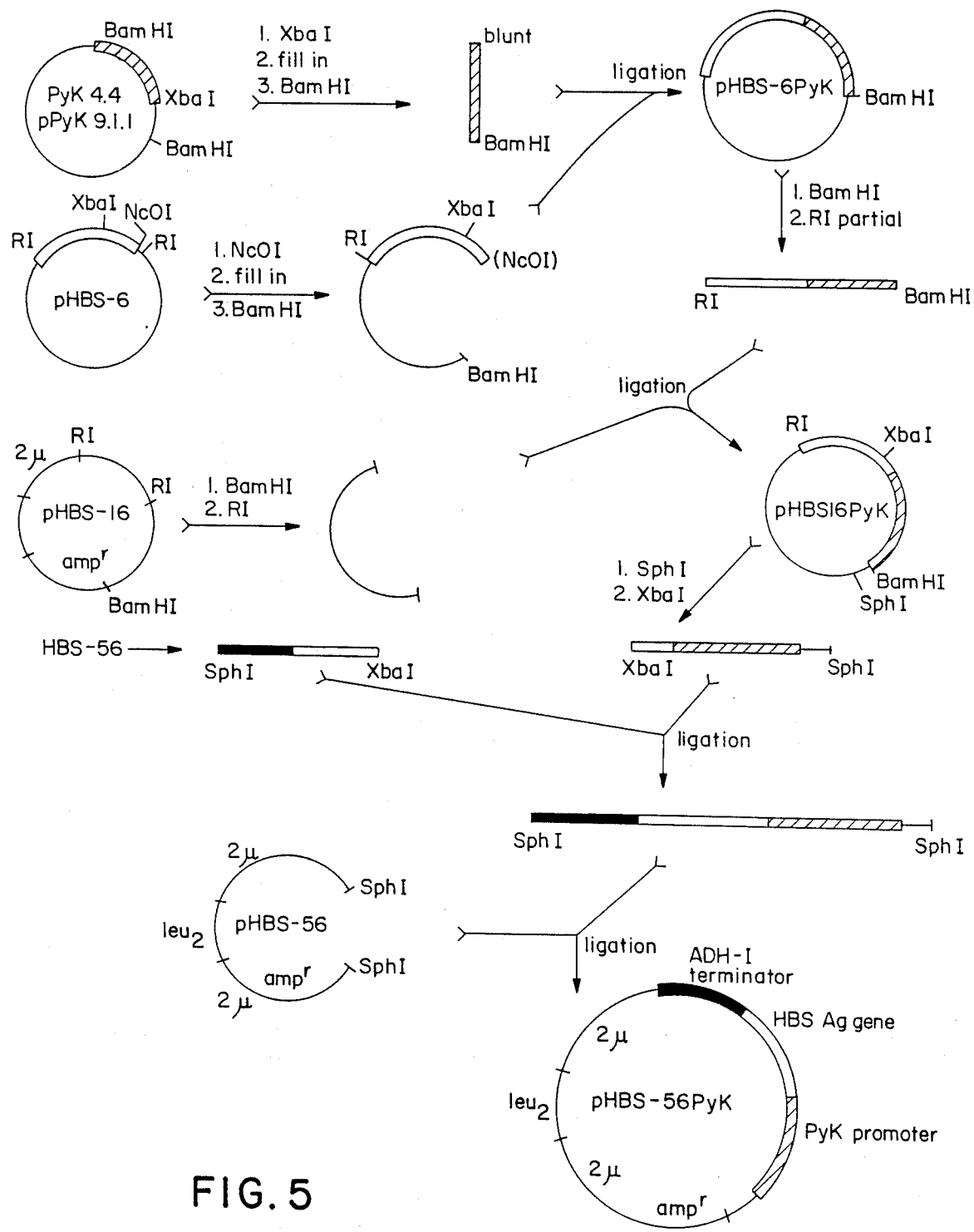
FIG. 5: Construction of a yeast expression plasmid containing the PyK promoter region.

Construction of yeast expression plasmids using the pyruvate kinase promoter region Two different constructions were made: pHBS16PyK and pHBS56PyK. The procedures are outlined in FIG. 5.

The plasmid pPyK 9.1.1, which contains the yeast PyK gene cloned in pBR322 was digested with XbaI and the protruding ends filled in with deoxynucleotides using DNA polymerase I. The product was digested with BamHI to finally isolate a 912 bp BamHI-blunt fragment containing the PyK promoter and 8 bases from the PyK coding region. This fragment was ligated to plasmid pHBS6 (contains the HBsAg gene, in which the 5' non-coding region has been deleted, cloned in pBR322, described in Example 8) previously digested with NcoI, filled in using DNA polymerase and digested with BamHI. After transformation of E. coli, pHBS6PyK was isolated. This plasmid contains the PyK promoter with codons for 3 extra amino acids fused in phase with the HBsAg coding sequence,

ATGTCTAG CATG.

pHBS6PyK was digested with BamHI to completion and partially digested with EcoRI to isolate a 1750 bp BamHi-EcoRI fragment containing the PyK promoter fused to the HBsAg gene. This 1750 bp fragment was ligated to the large fragment obtained after digestion of pHBS16 (ATCC Accession No. 40043, plasmid described in U.S. patent application Ser. No. 442,687, filed on or about Nov. 18, 1982, titled "Adenovirus Promoter in Yeast", herein incorporated by reference), with BamHI and EcoRI and used to transform E. coli. The yeast expression plasmid pHBS-16PyK was obtained. pHBS-16PyK was digested to completion with SphI and XbaI and a 1200 bp SphI-XbaI fragment (containing 200 bp of pBR322, the PyK promoter and 100 bp of the 5' region of the HBsAg gene) was isolated. This 1200 bp SphI-XbaI fragment was ligated to a 1070 bp XbaI-SphI fragment (isolated from pHBS-56) containing the 3' end of the HBsAg gene and the ADH-1 terminator. After digestion with SphI, a SphI-SphI 2300 bp fragment (cassette) containing the PyK promoter, HBsAg gene and ADH-1 terminator was isolated. This cassette fragment was cloned in pHBS-56 1 which had been previously digested with SphI. The yeast expression plasmid pHBS56 PyK (ATCC Accession No. 20666) was obtained. This plasmid was used to transform yeast strain AB102 (see Example 2) or strain 2150-2-3 (see Example 2).

EXAMPLE 7

Synthesis of HBsAg in yeast under PyK promoter control

One hundred ml cultures of strain AB102 containing plasmid pHBS56 PyK were grown to optical densities at 650 nm of 1-2. Cell-free lysates were prepared by agitation with glass beads and removal of cell debris by centrifugation. HBsAg was measured by the Abbott AusriaII radioimmunoassay and protein concentration was determined by the Coomassie blue binding method.

The results are shown in Table 2. They indicate that PyK promoter is at least two times more efficient than the ADH1 promoter for expression of protein product in yeast.

TABLE 2

Synthesis of HBsAg in yeast (a) from pHBS56 (control, ADH-I promoter).

| Exp # | sAg (μg/ml) | protein (mg/ml) | Spec. Activity (μgsAg/mg protein) |
|---|---|---|---|
| 1 | 8.2 | 24 | 0.34 |
| 2 | 7.2 | 24 | 0.32 |
| 3 | 4.7 | 27 | 0.23 |

(b) from pHBS56 PyK (PyK promoter)

| Exp # | sAg (μg/ml) | protein (mg/ml) | Spec. Activity (μgsAg/mg protein) |
|---|---|---|---|
| 1 | 18 | 2.5 | 0.68 |
| 2 | 10.6 | 22 | 0.48 |
| 3 | 15.2 | 27 | 0.56 |

Similar results were obtained by substituting yeast strain 2150-2-3 for yeast strain AB102 and repeating Example 7.

EXAMPLE 8

Construction of GAL regulator GAPDH promoter containing plasmids

Plasmid pLGSD5 is prepared as described in Guarente et al., (1982) supra. The plasmid was manipulated as follows: After restriction with XhoI, the overhangs were filled in with the Klenow fragment of DNA polymerase I ("Klenow fragment"), ligated with EcoRI linkers (GGAATTCC) and then completely digested with EcoRi and Sau3A to provide a 370 bp fragment which was isolated by gel electrophoresis and included the intergenic sequence between GAL1 and GAL10 genes of yeast, and provides for the GAL4 regulation sequence of the GAL1 and GAL10 genes.

This fragment was inserted into pBR322 which had been completely digested with EcoRI and BamHI, followed by treatment with alkaline phosphatase to prevent oligomerization. The resulting plasmid pBRGAL4 was treated in two different ways.

In the first procedure pBRGAL4 was completely digested with Sau3A, the overhangs filled in with the Klenow fragment, and the resulting blunt-ended fragment ligated with SalI linkers (CGTCGACG), followed by digestion with SalI and XhoI. The resulting 370 bp fragment was isolated by gel electrophoresis. This fragment has the original 370 bp yeast GAL4 regulator sequence with XhoI and SalI termini.

The second fragment was obtained by complete digestion of pBRGAL4 with XhoI and SalI to provide a XhoI-SalI fragment which included the 370 bp yeast GAL4 regulator sequence as well as about 280 bp of pBR322, the GAL4 sequence extending from Sau3A to SalI.

The two fragments were then cloned in the plasmid plot5. plot5 was prepared by inserting the 40 bp polylinker fragment of the following sequence

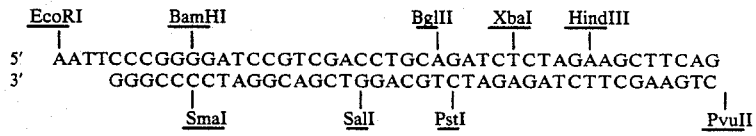

into pBR322 as an EcoRI-PvuII substitution followed by insertion of the trp-lac promoter (Russell and Bennett, Gene (1982) 20:231-245) into the PvuII site with transcription oriented toward the polylinker sequence. plot5 was completely digested with SalI, followed by treatment with alkaline phosphatase and the 370 bp and 650 bp fragments independently inserted into plot5 to provide plasmids plot5GAL4/370 and plot5-GAL4/650, respectively. Each of the plasmids was then completely digested with BamHI and SalI to reproduce the individual fragments extended by 6 bp of the polylinker fragment. These fragments were then ligated into pCI/1, which had been completely digested with BamHI and SalI followed by treatment with alkaline phosphatase to prevent recircularization. Plasmid pCI/1 is a derivative of pJDB219 (Beggs, Nature (1978) 275:104) in which the region corresponding to bacterial plasmid pMB9 in pJDB219 has been replaced by pBR322 in pCI/1. The resulting plasmids were designated pCI/1GAL4/370 and pCI/1GAL4/650, respectively. The BamHi-SalI fragment is located in the pBR322 portion of the vector pCI/1.

The next construction develops a hybrid promoter for expression of the Hepatitis B surface antigen (HBsAg), employing the RNA polymerase binding region of GAPDH. The previously prepared plasmid pHBS56/16-3, a yeast shuttle vector containing the alcohol dehydrogenase 1 (ADH1) promoter, the HBsAg gene and ADH terminator as a SphI fragment, was digested with SphI and the ends modified with Bam linkers. The Bam linkers have the sequence CGGATCCG.

pHBS56/16-3 was prepared as follows: A TaqI-HpaI fragment obtained from the HBsAg coding region which included 26 bp of the pre-sAg region, 681 bp of the sAg region and 128 bp of the 3'-untranslated region, was linked with EcoRI linkers and cloned at the EcoRI site in pBR322. The EcoRI linkers have the sequence GGAATTCC. The plasmid pHBS5 was thus obtained.

After digesting pHBS5 with EcoRI, the digest was resected with Bal31 and religated with EcoRi linkers (GGAATTCC). After digestion with EcoRI the material of about 800 bp was isolated from a polyacrylamide gel. This isolate was then recloned into pBR322 which had been digested with EcoRI and treated with alkaline phosphatase. Where the resection was to the sequence CATGG, which included the methionine codon, the EcoRI linker created an NcoI site. The plasmids were screened for the presence of an NcoI site and one of the plasmids chosen for further manipulation. This plasmid, designated pHBS5-3, was restricted with EcoRI, the EcoRI fragment made blunt-ended with Klenow fragment and dNTPs, and the blunt-ended fragment was then restricted with XbaI to provide an about 100 bp fragment having an XbaI overhang and blunt end at the former EcoRI site.

pHBS5 was then digested with ClaI, made blunt-ended with the Klenow fragment and dNTPs, digested with XbaI, followed by alkaline phosphatase treatment. The 100 bp fragment was then inserted into the vector to provide the plasmid pHBS6. Upon sequencing of the blunt-ended ligation site, it was found that an adenosine had been lost, so as to lose the EcoRI site, where the sequence was now ATCGATTCCCATGG. The ClaI and NcoI sites were retained. The loss of the A resulted in pHBS6 having a single EcoRi site.

pHBS5-3 was digested with EcoRI and the resulting EcoRI fragment having the sAg fragment isolated by gel electrophoresis and inserted into the vector pHBS16 (Valenzuela et al., *Nature* (1982) 298:347-350). This plasmid has the ADH1 promoter and the sAg gene in an EcoRI fragment in a plasmid containing the 2 μm origin, a TrpI gene and pBR322. The plasmid was digested with EcoRI, treated with alkaline phosphatase to prevent recircularization, and the EcoRI fragment from pHBS5-3 inserted to provide pHBS16-3, where the sAg gene isolated as a TaqI-HpaI fragment had been modified by Bal31 resection. The plasmid pHBS16-3 was digested with SphI and XbaI to provide a fragment which had the ADH promoter at the Sph terminus and the 5'-end of the sAg gene.

A 1.1 kb fragment having the ADH terminator region and the 3'-portion of the sAg gene was obtained from pHBS56. pHBS56 was constructed as follows. The active portion of the ADH1 promoter region is contained within the SphI-HindIII fragment of approximately 300 bp (Bennetzen et al., *J. Biol. Chem.* (1982) 257:301). The SphI site in the ADH promoter begins at position −413 and the yeast terminator sequence is contained within a HindIII-SphI fragment of about 330 bp. In each case the SphI site is distal to the coding region. A 1500 bp ADH1 promoter fragment terminating at position −9 (Hitzeman et al., *Nature* (1981) 293: 717) and an approximtely 450 bp terminator unit from nucleotides 913 to 1368 in the ADH gene nucleotide sequence were joined at a HindIII site between the fragments and cloned into the BamHI site of the vector YEp13 (Broach and Hicks, *Gene* (1979) 8: 121) to provide pADH5.

The HBsAg-DNA segment of pHBS5 was excised by EcoRI digestion, blunt-ended with the Klenow fragment and joined at both ends with HindIII linkers, CAAGCTTG. After digestion with HindIII, the HBsAg fragment was inserted into the HindIII site of the plasmid pADH5 which had been digested at the HindIII site intermediate the ADH1 promoter and terminator sequence. A plasmid with the HBsAg gene in the correct orientation as determined by restriction analysis was designated pHBS22. The cassette was included between two SphI restriction sites. pHBS22 was digested with SphI to obtain a fragment of about 1500 bp and inserted into SphI digested pC1/1 to provide pHBS56 which was cloned in *E. coli* HB101.

pHBS56 was digested with SphI and XbaI to provide a 1.1 kb fragment having the ADH terminator region and the 3'-portion of the sAg gene with the SphI site proximal to the terminator region. The 1.1 kb SphI-XbaI fragment was joined to the SphI-XbaI fragment from pHBS16-3, which resulted in providing the complete sAg gene in the correct orientation between the ADH promoter and terminator. This SphI-SphI fragment was ligated to SphI digested pHBS56, replacing the cassette of pHBS56 to provide the plasmid pHBS56/16-3 with the resected sAg coding region fragment. The cassette was then excised from pHBS56/16-3 by digestion with SphI, followed by chewing back the overhangs with the Klenow fragment in the presence of dNTPs, then ligated with BamHI linkers, followed by digestion with BamHI to provide a 1.6 kb fragment which was isolated by gel electrophoresis. The fragment included the ADH promoter region, the sAg gene and ADH terminator region, as described above. This fragment was inserted into the BamHI site of pBR322 to provide pPGT16-3 which was digested with BamHI and XbaI and the resulting 1.1 kb fragment gel isolated, where the XbaI-BamHI fragment had the 3' portion of the sAg gene and the ADH terminator region.

pHBS6 was digested with XbaI and NcoI and the 94 bp fragment gel isolated to provide the 5'-portion of the sAg gene. A synthetic adapter was prepared of the formula

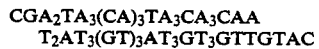

having TaqI and NcoI termini and providing the −25 to −1 nucleotides of the GAPDH (GAP49) promoter and the initiation condon of the sAg gene. This synthetic fragment, the NcoI-XbaI fragment, and the XbaI-BamHI fragment were ligated simultaneously, followed by digestion with TaqI and BamHI. The resulting fragment was then substituted into pBR322 linearized with ClaI and BamHI, followed by treatment with alkaline phosphatase. The resulting plasmid, which contains the −1 to −25 bp of the GAPDH promoter region, the sAg gene, and the ADH terminator, where the NcoI restriction site is lost was called pHBS6LGAPsAgtADH.

pGAP1, a plasmid prepared by insertion of a HindIII fragment containing the GAPDH gene GAP49 (Holland and Holland, *J. Biol. Chem.* (1979) 254: 5466-5474) inserted in the HindIII site of pBR322, was digested with HinfI and a 500 bp promoter containing fragment isolated. The fragment was resected with Bal31 to remove about 50 or 90 bp, followed by ligation with HindIII linkers and digestion with HindIII. pBR322 was digested with HindIII, followed by treatment with alkaline phosphatase and the about 450 or 410 bp fragment inserted to provide pGAP128 and pGAP396, respectively.

pGAP128 was digested with HindIII, the fragment made blunt-ended with the Klenow fragment and dNTPs and the resulting 450 bp fragment isolated by gel electrophoresis. This fragment was inserted into SmaI digested plot5, which had been treated with alkaline phosphatase, to provide plasmid plot5pGAP128, which contained about −400 to +27 bp of the GAPDH promoter and coding region. Plasmid plot5-pGAP396 was prepared from pGAP396 in an identical manner and thus differs from plasmid plot5pGAP128 in having about 15-30 fewer bp at each terminus of the GAPDH promoter region (about −385 to −3).

Plasmids GAP1-GAP4 were then prepared in the following manner. Plasmid plot5pGAP128 was digested with TaqI and BamHI to provide an about 390 bp TaqI-BamHI fragment which included the −26 to about −400 bp of the GAPDH promoter region and a portion of the HindIII and plot5 polylinker. pHBS6LGAPsAgtADH plasmid was also digested with TaqI and BamHI and a 1.1 kb TaqI-BamHI fragment containing the 3'-terminus of the GAPDH promoter region, the sAg gene and the ADH terminator region was gel isolated and ligated to the other TaqI-BamHI fragment to provide a BamHI-BamHI fragment which included approximately 400 bp of the GAPDH promoter region, the sAg gene in proper orientation for transcriptional regulation by the GAPDH promoter, followed by the ADH terminator region. This fragment was ligated into pBR322 which had been digested with BamHI and treated with alkaline phosphatase to provide plasmid pPGT80. This BamHI cassette could now be isolated and inserted into plasmid pC1/1, at the BamHI site in the pBR322 portion of pC1/1, where in plasmid GAP1 the ADH terminator region is proximal to the amp$^r$ gene with the pBR322 portion divided into an approximately 4 kb sequence including the amp$^r$ gene and a 375 bp region separating the cassette from the 2 μm sequences. In GAP2, the promoter is adjacent to the long pBR322 sequence with transcription in the same direction as the amp$^r$ gene. The same cassette was inserted into BamHI-digested pC1/1GAL4/650 to obtain plasmids GAP3 and GAP4, where GAP3 has the GAPDH promoter distal from the GAL4 regulator region and the long pBR322 sequence and GAP4 has the GAPDH promoter adjacent to the GAL4 regulator region, which is adjacent to the long pBR322 sequence.

Figure 6:
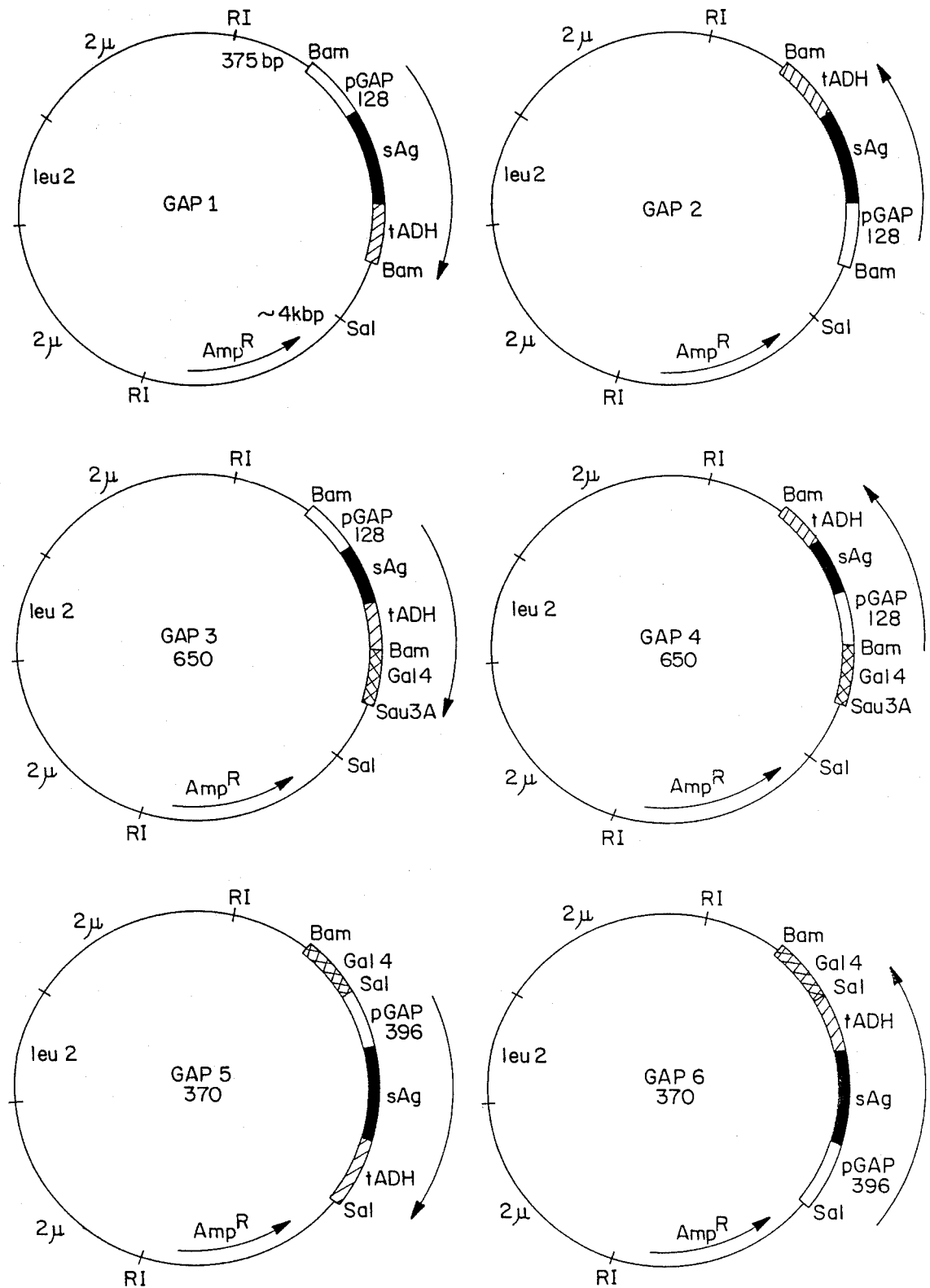
FIG. 6 is a diagrammatic view of plasmids GAP1-6.

Plasmids GAP5 (ATCC Accession No. 20705) and GAP6 were isolated as follows. Plasmid plot5pGAP396 was digested with SalI and TaqI and a fragment containing 9 bp of the plot5 polylinker sequence and the GAPDH promoter sequence extending from about −385 to −26 bp was isolated. An approximately 130 bp TaqI-XbaI fragment including −25 to −1 bp of the GAPDH promoter and +1 to +93 bp of the sAg gene was obtained from pHBS6LGAPsAgtADH. A 1.1 kb XbaI-SalI fragment containing the 3'-portion of the sAg gene and the ADH terminator as well as 6 bp of plot5 polylinker sequence was obtained from plasmid plot5-sAgtADH (described below—Pyruvate Kinase Promoter). These three fragments were ligated, digested with SalI and then cloned into SalI-digested pC1/1GAL4/370. GAP5 has the GAPDH promoter region adjacent to the GAL4 regulator region, which is proximal to the short pBR322 sequence, and GAP6 has the GAPDH promoter region distal from the GAL4 regulator region and proximal to the long pBR322 sequence (see FIG. 6).

EXAMPLE 9

Construction of GAL regulator, Pyk promoter containing plasmids

Plasmid pHBS6Pyk containing the sAg gene under the transcriptional regulatory control of the Pyk promoter was obtained by cloning a 4.4 kb insert of yeast genomic DNA in pBR322 containing the Pyk gene and 911 nucleotides of 5'-untranslated region, and digestion of this plasmid pPyk9.1.1 with XbaI. After making the ends blunted-ended, the linear fragment was digested with BamHI providing a 912 bp BamHI-blunt fragment containing the Pyk promoter and 8 bases from the Pyk coding region. This fragment was inserted into the plasmid pHBS6, which had been digested with NcoI, blunt-ended and digested with BamHI. The plasmid pHBS6Pyk was totally digested with EcoRI, to obtain a fragment including the sAg gene and a portion of the Pyk promoter region. The fragment was made blunt-ended with the Klenow fragment and dNTPs, followed by ligation to BamHI linkers, digested with XbaI, which is internal to the sAg gene, the XbaI terminus made blunt-ended with the Klenow fragment and dNTPs, followed by digestion with BamHI, to provide a 580 bp BamHI-blunt-ended (XbaI) fragment. The plasmid plot5 was digested with EcoRI, made blunt-ended, digested with BamHI and treated with alkaline phosphatase and the two fragments joined to provide plasmids plot5PyksAg51 and plot5PyksAg57. The two differ in that the BamHI site of the latter was not regenerated during cloning, possibly as a consequence of minimal nuclease contamination (digestion).

plot5 was treated as previously described (EcoRI digestion, blunt-ended, BamHI digestion and treatment with alkaline phosphatase) and joined to a 1.1 kb fragment obtained by digestion of pGT16-3 with XbaI, followed by blunt ending, followed by digestion with BamHI and gel isolation. This fragment was introduced into plot5 to provide the plasmid plot5sAgtADH. Again the BamHI site in this plasmid was not regenerated, presumably due to digestion by contaminating nuclease.

Plasmids Pyk1 and Pyk2 were prepared as follows. Plasmid plot5PyksAg51 was digested with BamHI, then with XbaI, and an approximately 580 bp fragment containing about 480 bp of Pyk promoter and 93 bp of the 5'-end of the sAg gene was gel isolated. A 1.1 kb XbaI-SalI fragment containing the 3'-portion of the sAg gene, the ADH terminator and about 6 bp of the plot5 polylinker was isolated from plot5AgtADH. These two fragments were ligated, digested with BamHI and SalI and then cloned into plasmid pC1/1, which had been cleaved with BamHI and SalI and treated with alkaline phosphatase, to yield plasmid Pyk1. Plasmid Pyk2 was prepared similarly but the 580 bp SalI-XbaI, Pyk promoter/HBsAg gene 5'-end fusion fragment was isolated with plot5PyksAg.57 and included about 6 bp of plot5 polylinker sequence upstream from the promoter region. Also the 1.1 kb XbaI-BamHI fragment containing the 3'-part of the HBsAg gene and the ADH terminator was derived from plasmid pGT16-3.

Plasmids Pyk3–Pyk6 were prepared as follows. Plasmid plot5PyksAg51 was digested with BamHI, then with XbaI and the about 580 bp fragment containing the Pyk promoter and the 5'-part of the HBsAg gene isolated as above. The 1.1 kb BamHI-XbaI fragment, containing the 3'-portion of the HBsAg gene and ADH terminator, was recovered from pGT16-3, also as above, and the two fragments ligated, digested with BamHI and inserted with different orientations into the BamHI site of pC1/1GAL4/650 (Pyk3, Pyk4). Plasmids Pyk5 (ATCC Accession No. 20706) and Pyk6 were prepared similarly except that the SalI-XbaI fragment containing the Pyk promoter and 5'-end of the sAg gene was isolated from plot5PyksAg.57 and the XbaI-SalI sAg gene 3'-portion/ADH terminator fusion fragment was derived from plot5sAgtADH and thus both fragments included approximately 6 bp of plot5 polylinker sequence. The cassette so formed was then cloned into the SalI site of pC1/1GAL4/370 in opposite orientations.

Figure 7:
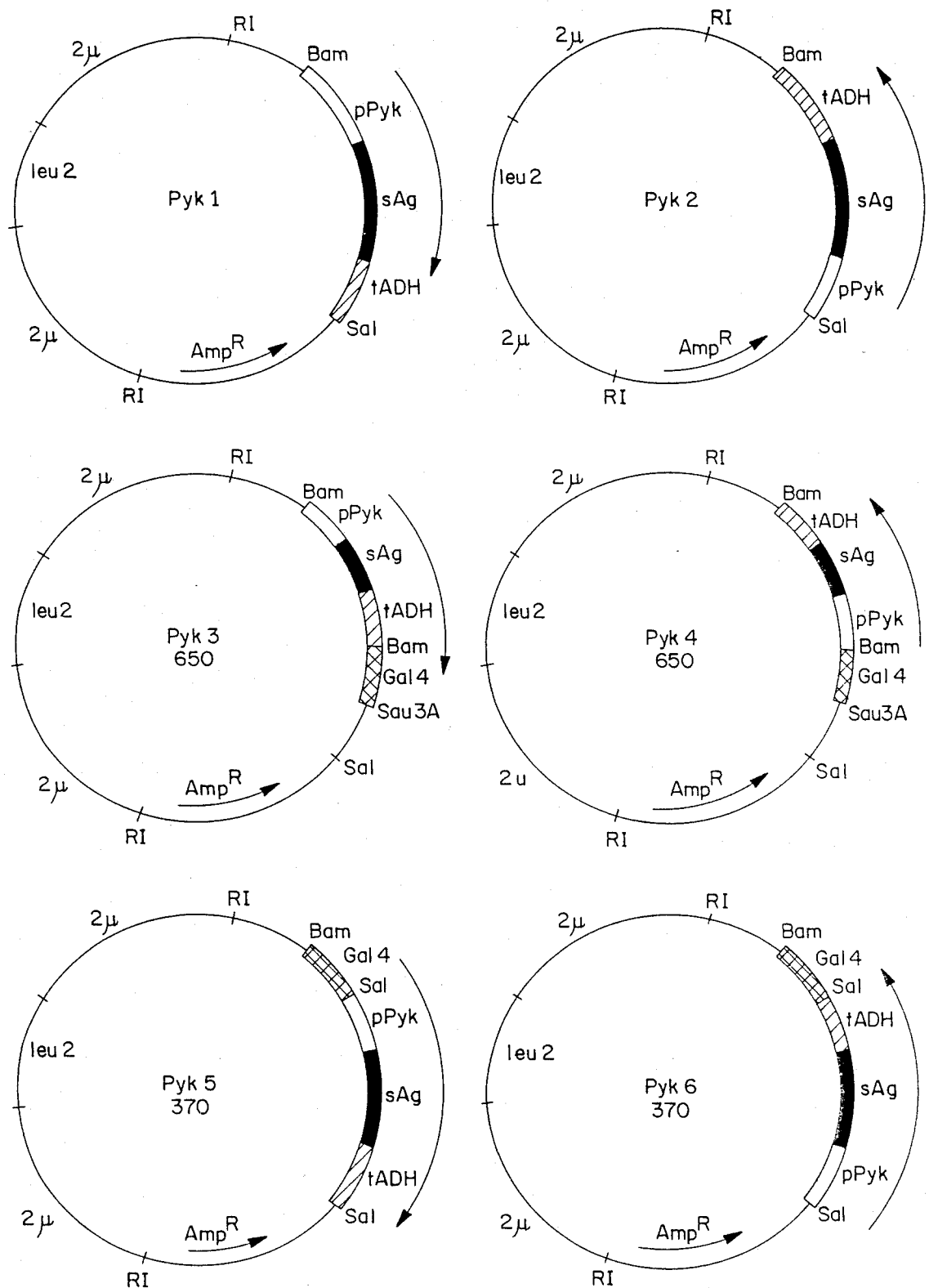
FIG. 7 is a diagrammatic view of plasmids PyK1-6.

The six plasmids designated Pyk1-6 (see FIG. 7) are distinguished by Pyk1 having the promoter region proximal to the short pBR322 sequence; Pyk2 having the promoter region proximal to the long pBR322 sequence; Pyk3 having the promoter region proximal to the short pBR322 sequence and distal from the GAL4 sequence; while Pyk4 has the promoter region proximal to the GAL4 region, which in turn is proximal to the long pBR322 sequence; Pyk5 has the promoter region proximal to the GAL4 region which is proximal to the short pBR322 sequence; while Pyk6 has a promoter region distal from the GAL4 region and proximal to the long pBR322 sequence.

These plasmids described above were transformed into *S. cerevisiae* strain 2150-2-3 (available from Lee Hartwell, University of Washington) under conventional conditions (Hinnen et al., *Proc. Natl. Acad. Sci. USA* (1978) 75: 1929–1933). Cultures of 50–150 ml were grown to mid or late log phase in rich media (YEP) under neutral conditions (3% glycerol, 2% lactic acid), and then inducing conditions (+2% galactose), or repressing conditions (+2% glucose) for the final 1–2 generations. After lysis with glass beads and clarification of the supernatants by centrifugation, HBsAg expression was determined as described above. The results for the 12 plasmids are set forth in the following Table 3.

TABLE 3

Expression of HBsAg from Gal Regulated Hybrid Promoters

| Construction | YEP + Glycerol/ Lactic acid μg sAg/mg protein | YEP + Galactose μg sAg/mg protein | YEP + Glucose μg sAg/mg protein | Induction (Gal/glycerol lactic acid) |
|---|---|---|---|---|
| GAP1 | 0.04 | 0.09 | 0.02 | 2.0 |
| GAP2 | 1.65 | 0.8 | 1.4 | 0.5 |
| GAP3 | 0.25 | 0.30 | — | 1.2 |
| GAP4 | 0.10 | 0.75 | — | 7.5 |
| GAP5 | 0.25 | 2.1 | — | 8.4 |
| GAP6 | 1.55 | 1.4 | 1.0 | 0.9 |
| PYK1 | 0.10 | 0.30 | 0.14 | 3.0 |
| PYK2 | 1.65 | 1.4 | 1.1 | 0.85 |
| PYK3 | 0.10 | 0.15 | — | 1.5 |
| PYK4 | 0.10 | 1.0 | 0.05 | 10.0 |
| PYK5 | 0.03 | 1.4 | 0.02 | 47.0 |
| PYK6 | 1.7 | 1.8 | 0.9 | 0.9 |

EXAMPLE 10

Construction of pPGAP

A yeast expression vector was prepared called pPGAP having a polyrestriction site linker between the GAPDH terminator and short promoter region. Plasmid plot5pGAP128 (described in Example 9) was digested with BamHI and TaqI to yield an approximately 390 bp BamHI-TaqI fragment having the −400 to −26 bp of the GAPDH promoter. The BamHI-TaqI fragment was ligated to a synthetic fragment having the following sequence:

$$CGA_2TA_3(CA)_3TA_3CA_3CACCATG_3A_2T_2CGT_2AG_2$$
$$T_2AT_3(GT)_3AT_3GT_3GTGGTAC_3T_2A_2GCA_2TC_2AGCT$$

to provide a BamHI-SalI fragment, which was digested with BamHI and SalI and used to replace the BamHI-SalI fragment of BamHI-SalI digested pBR322 treated with alkaline phosphatase. After ligation, the plasmid pGAPNRS was obtained which was digested with BamHI and SalI to provide a 400 bp BamHI-SalI fragment which was gel isolated. This fragment was ligated to an about 900 bp SalI-BamHI fragment containing the GAPDH terminator region and a short segment of 3' coding region and the resulting 1.4 kb BamHI-BamHI fragment digested with BamHI. The SalI-BamHI GAPDH terminator fragment was obtained by SalI and BamHI digestion of pGAP2, a plasmid prepared by insertion of an about 3.3 kb BamHI fragment containing the GAPDH gene GAP49 (Holland and Holland, supra) into the BamHI site of pBR322. Plasmids pGAP2 and pGAP1 were obtained as follows as previously described in Example. Briefly, a yeast gene library was prepared by inserting fragments obtained after partial digestion of total yeast DNA with restriction endonuclease Sau3A in lambda-phage Charon 28 (Blattner et al., *Science* (1977) 196: 161–169). The phage library was screened with DNA complementary to the yeast GAPDH mBNA and the yeast GAPDH gene from one of these clones was subcloned as either an about 3.3 kb BamHI fragment in the BamHI site of pBR322 (pGAP-2) or as an about 2.1 kb HindIII fragment in the HindIII site of pBR322 (pGAP-1).

pBR322 was digested with EcoRI and SalI, the termini blunt-ended and ligated to BamHI linkers, followed by BamHI digestion and the BamHI-BamHI 3.8 kb fragment gel isolated, recircularized by self-ligation, cloned and designated pBRΔR1-Sal. The 1.4 kb BamHI-BamHI fragment was inserted into the BamHI-digested, alkaline phosphatase treated pBRΔR1-Sal vector to provide the plasmid pPGAP of about 5.3 kb with the orientation in the opposite direction of the amp$^r$.

EXAMPLE 11

Cloning and expression of hSOD

Molecular cloning of hSOD cDNA

Total RNA was prepared from an adult human liver by the guanidinium thiocyanate/lithium chloride method (Cathala et al., *DNA* (1983) 2: 329–335). polyA RNA was used to synthesize double-stranded cDNA (Maniatis et al., *Molecular Cloning*, 213–242, Cold Spring Harbor, 1982) and this was passed over a Sepharose CL4B column to enrich for cDNAs of greater than 350 bp (Fiddes and Goodman, *Nature* (1979) 281: 351–356). The cDNA was inserted at the PstI site of plot4, a pBR322 derivative having the following sequence replacing the PstI-EcoRI site.

```
      PstI     HinfI              AluI
1    GGTGAATCCGTAATCATGGTCATAGCTGTTTCCTGTGTGAAATTGTTATCCGCTC
     ACGTCCACTTAGGCATTAGTACCAGTATCGACAAAGGACACACTTTAACAATAGGCGAG
     HphI HindIIAluI
60   ACAATTCCACACATTATACGAGCCGATGATTAATTGTCAACAGCTCATTTCAGAATATTT
     TGTTAAGGTGTGTAATATGCTCGGCTACTAATTAACAGTTGTCGAGTAAAGTCTTATAAA EcoRI
120  GCCAGAACCGTTATGATGCGG
     CGGTCTTGGCAATACTACGCCTTAA
```

The cDNA insertion employed the oligo-dG:dC tailing method (Maniatis et al., supra). *E. coli* strain D1210 was transformed with this mixture and transformants selected on L-agar containing 10 μg/ml tetracycline (Kushner, S. R. (1978) In: *Genetic Engineering*, eds. Boyer, H. B. and Nicosia, S., (Elsevier/North Holland, Amsterdam) p. 17). Plasmid DNA constituting a liver cDNA library was prepared (Maniatis et al., *Molecular Cloning*, pp. 86-94, Cold Spring Harbor 1982) directly from approximately 62,000 recombinant colonies plated at a density of approximately 3,000 colonies per 9 cm diameter Petri dish.

Isolation of r-hSOD clones

Strain D1210 was retransformed wtih the liver cDNA library and about 40,000 clones were grown on nine 14 cm diameter Petri dishes. After transfer of the colonies to nitrocellulose paper and chloramphenicol amplification of plasmid DNA, the cells were lysed and the filters prepared for hybridization (Ish-Horowicz and Burke, *Nucleic Acids Research* (1981) 9: 2989-2998). Oligonucleotide probes were employed for screening by hybridization, with the probes consisting of enzymatically-radiolabeled, chemically-synthesized DNA molecules complementary to the mRNA encoding amino acid residues 19 to 24 of the protein (Jabusch et al., supra.; Barra et al., supra.); the mixture had the following sequences:

```
3' TTA AAA CTT GTT TTT CT 5'
    G        G   C   C   C
``` where all of the indicated possibilities for encoding the peptide sequence were prepared (32-fold degenerate).

The probes were labeled with $^{32}$P to a specific activity of $1$-$3 \times 10^8$ cpm/μg and Millipore (0.45 μm) filtered before use. Filters were prehybridized for 6 hrs at 30° C. in 4×SSC, 2×Denhardts's solution, 40 mM sodium phosphate, pH 7.5, 300 μg/ml sonicated salmon testes DNA. Hybridization was for 20 hrs at 30° C. in the same solution containing $2 \times 10^6$ cpm/ml hSOD DNA probe (residues 19-24). Filters were washed in 4×SCC, once for 15 min at r.t. and twice for 15 min at 30° C., blotted dry and autoradiographed with an intensifying screen for 24 hrs at −70° C.

Areas on the master plates that corresponded to duplicate positive signals were picked into L-broth and plasmid DNA prepared by the miniscreen procedure (Maniatis et al., *Molecular Cloning*, 178, 368-369, Cold Spring Harbor 1982). This DNA was cut with PstI and subjected to Southern blot analysis (Southern, *J. Mol. Biol.* (1975) 98: 503-517) hybridizing initially with the previous labeled probes (amino acid residues 19-24) and then with additional radiolabeled probes derived from amino acid residues 109-114 and having the following sequences (all possible variations, 72-fold degenerate) present as a mixture:

```
3' CTA GTA ACA TAA TAA CC 5'
    G   G   G   G   G
            T       T
```

One plasmid pool contained a cDNA insert of 520 bp that hybridized with both probes and after colony purification, plasmid DNA was prepared from this clone and sequenced by the method of Maxam and Gilbert (*Proc. Natl. Acad. Sci. USA* (1977) 74: 560-564). The hSOD cDNA clone pSOD1 constitutes the coding region for amino acids 10-153 of hSOD, a single translational stop codon and a 3' untranslated region. Therefore, in the expression vector construct, the base sequence of the region encoding amino acids 1-9 is derived from the published amino acid sequence of hSOD (Jabusch et al., supra; Barra et al., supra) and synthesized chemically as a part of the variable linker segment (see discussion relating to FIG. 8).

Construction of plot5 derivatives containing r-hSOD

Figure 8:
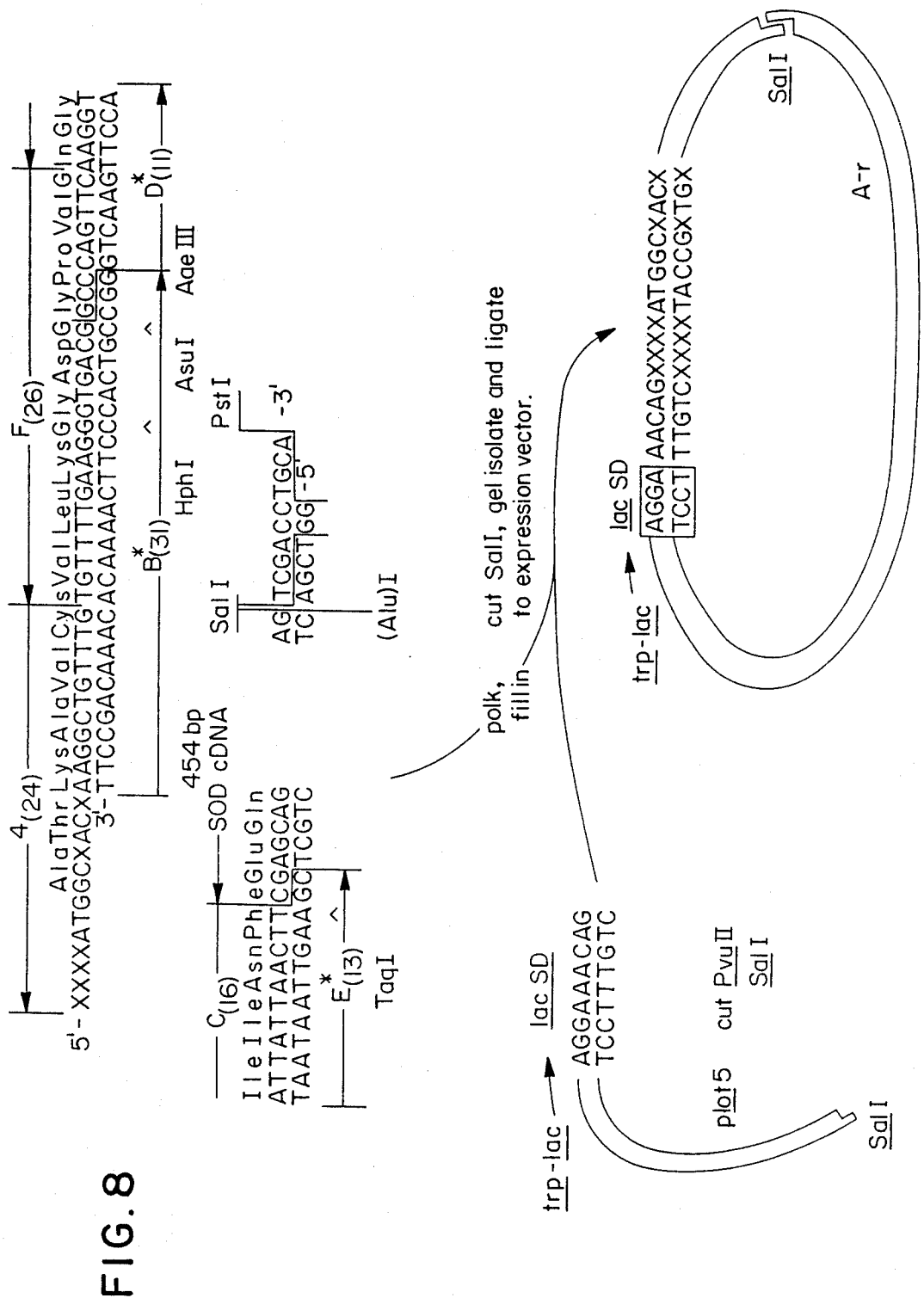
FIG. 8 indicates the DNA linker sequence and a flow diagram showing its use in a construct for hSOD.

The synthetic DNA molecules F(26), C(16), B(31), D(11), E(13) and 4(24) shown in FIG. 8, were synthesized by the phosphoramidite method.

The single strand 4(24) was prepared by using all four bases, at each site where X is indicated. Furthermore, silica was withdrawn from the synthesis of the 24mer, such that single-stranded 21mers, 22mers, and 23mers are obtained in addition to the 24mers. After removal from the silica support, the four mixtures are combined in appropriate proportions to provide for equimolar amounts of each of the possible single strands. This mixture was treated as a single product in the subsequent steps.

Molecules F(26), C(16), B(31) and D(11) were mixed together in equimolar amounts and 10 μg phosphorylated using T4 polynucleotide kinase. After phenol-ether extraction, the additional non-phosphorylated synthetic DNA molecules 4(24) and E(13) were added, such that all fragments were equimolar. The equimolar mixture contained 13 μg of DNA in 133 μl of 0.3×kinase buffer.

After annealing by cooling at a uniform rate from 70° C. to 20° C. over 60 min, the single strands were ligated together with T4 ligase in 200 μl ligation mix at 14° C. for 4 hrs, phenol-chloroform extracted, ethanol precipitated and the 5'-ends of 4(24 ) and E(13) phosphorylated using T4 polynucleotide kinase (Maniatis et al., supra). Preparative polyacrylamide gel electrophoresis was used to isolate the completely ligated 53 bp material having 5'- and 3'-overhangs.

The above purified fragment mixture was then ligated to the 460 bp TaqI-PstI segment of the hSOD cDNA as shown in FIG. 8. This segment was itself constructed by isolating the 454 bp TaqI-AluI hSOD fragment, making it flush-ended using Klenow and inserting it into plot5 between its EcoRI and SalI sites which had been similarly made flush-ended. After preparation of plasmid DNA from this recombinant, the 460 bp TaqI-PstI hSOD fragment was isolated by preparative polyacrylamide gel electrophoresis. After extraction and precipitation, the 515 bp fragment resulting from the joining of the synthetic fragment to the 460 bp TaqI-PstI hSOD fragment was blunt-ended (525-528 bp) and then digested with SalI and the resulting 519-522 bp hSOD fragment isolated by polyacrylamide gel electrophoresis. This fragment was then inserted into plot5 which had been digested with PvuII and SalI and then treated with alkaline phosphatase. The resulting plasmids were used to transform *E. coli* strain D1210. (F−, lacI+, lacO+, lacZ+, lacY−, gal−, pro−, leu−, thi−, end−, hsm−, hsr−, recA−, rpsL−) Recombinants obtained after transformation of strain D1210 were selected on L-agar containing 100 μg/ml ampicillin to give a set of clones, which were screened for an NcoI site. One was selected and designated phSOD (also designated pSODNco5).

Construction of a yeast vector for SOD expression

The plasmid phSOD was digested with NcoI and SalI and a 550 bp fragment obtained, which included 1 nucleotide untranslated at the 5'-terminus and the entire coding region for hSOD. pPGAP was digested with NcoI and SalI followed by treatment with alkaline phosphatase and the SalI-NcoI fragment substituted for the NcoI-SalI fragment in pPGAP to provide pPGAP-SOD (ATCC Accession No. 20708). BamHI digestion of pPGAPSOD resulted in a 2 kb fragment which was gel isolated and inserted into the BamHI site of pC1/1 and pC1/1 GAL4/370. These plasmids were transformed into yeast strain 2150-2-3 as described previously, with the results of expression set forth in the following Table 4.

TABLE 4
Expression of Human SOD in Yeast Strain 2150

| Plasmid | Carbon Source | SOD[2] μg/mg protein |
|---|---|---|
| pC1/1 | g, L[1] | 0 |
| pC1/1GAPSOD | g, L | 148 |
| pC1/1GALGAPSOD | g, L | 0.4 |
|  | gal | 68 |

[1]All cultures grown in Minus Leucine media with 2% lactic acid, 3% glycerol with or without 2% galactose to late log or early stationary phase.
[2]Determined by RIA.

hSOD levels were measured using a standard radioimmunoassay with iodinated authentic hSOD as standard. Constitutive synthesis from the GAP promoter leads to very high levels of hSOD production, of the order of 10-30% of the total cell protein. The induction with galactose works almost as well, yielding about 7% of the cell protein as hSOD.

EXAMPLE 12

Cloning and expression of alpha-1-antitrypsin

A cDNA library was made from 10 μg of polyA+ RNA isolated from a part of a human liver. This library was prepared by oligo-dT priming of the first cDNA strand and self-priming of the second cDNA strand. The ds cDNA was size fractionated on a Sepharose Cl4B column and those molecules greater than 300 bp isolated. This fraction was treated with nuclease S1 and tailed with dCTP, using terminal transferase. The tailed cDNA was annealed to pBR322 which had been digested with PstI and tailed with dGTP. Transformation of E. coli HB101 yielded 60,000 colonies, where greater than 90% of the clones were recombinant.

Two synthetic oligonucleotide probes were used to isolate the alpha-1-antitrypsin ($\alpha_1$-AT) cDNA, the first probe corresponding to amino acid residues 344-350 near the C-terminus of the protein was used to probe 5,000 colonies and the second probe, corresponding to amino acid residues −23 to −17 (+1 being the first nucleotide of the first codon of the mature $\alpha_1$-AT) of the signal peptide, was used to probe 25,000 colonies. The probe sequences were taken from the partial nucleotide sequence described by Kurachi et al., *Proc. Natl. Acad. Sci. USA* (1981) 78: 6826; Leicht et al., *Nature* (1982) 297: 655). Approximately 3% of the colonies hybridized to the C-terminal probe and four hybridized to the N-terminal probe. The four N-terminal clones and 12 C-terminal clones were isolated and subjected to restriction analysis. From these, three overlapping clones which cover the entire cDNA were subjected to further study and were used to construct the full-length cDNA clone.

The entire sequence of a composite full length cDNA derived from the three plasmids is as follows:

```
                                                                   -24
                                                         Met Pro Ser Ser
                          GGGGGGGGGGGAGGGTAATCGACA ATG CCG TCT TCT
       -20                          -10                            -1
    Val Ser Trp Gly Ile Leu Leu Leu Ala Gly Leu Cys Cys Leu Val Pro Val Ser Leu Ala
    GTC TCG TGG GGC ATC CTC CTG CTG GCA GGC CTG TGC TGC CTG GTC CCT GTC TCC CTG GCT

1 Glu Asp Pro Gln Gly Asp Ala Ala Gln Lys Thr Asp Thr Ser His His Asp Gln Asp His
  1 GAG GAT CCC CAG GGA GAT GCT GCC CAG AAG ACA GAT ACA TCC CAC CAT GAT CAG GAT CAC
        BamHI

21 Pro Thr Phe Asn Lys Ile Thr Pro Asn Leu Ala Glu Phe Ala Phe Ser Leu Tyr Arg Gln
 61 CCA ACC TTC AAC AAG ATC ACC CCC AAC CTG GCT GAG TTC GCC TTC AGC CTA TAC CGC CAG

41 Leu Ala His Gln Ser Asn Ser Thr Asn Ile Phe Phe Ser Pro Val Ser Ile Ala Thr Ala
121 CTG GCA CAC CAG TCC AAC AGC ACC AAT ATC TTC TTC TCC CCA GTG AGC ATC GCT ACA GCC

61 Phe Ala Met Leu Ser Leu Gly Thr Lys Ala Asp Thr His Asp Glu Ile Leu Glu Gly Leu
181 TTT GCA ATG CTC TCC CTG GGG ACC AAG GCT GAC ACT CAC GAT GAA ATC CTG GAG GGC CTG

81 Asn Phe Asn Leu Thr Glu Ile Pro Glu Ala Gln Ile His Glu Gly Phe Gln Glu Leu Leu
241 AAT TTC AAC CTC ACG GAG ATT CCG GAG GCT CAG ATC CAT GAA GGC TTC CAG GAA CTC CTC

Arg(a,c)                                            Asp  Gly(c)
101 His Thr Leu Asn Gln Pro Asp Ser Gln Leu Gln Leu Thr Thr Gly Asn Gly Leu Phe Leu
301 CAT ACC CTC AAC CAG CCA GAC AGC CAG CTC CAG CTG ACC ACC GGC AAT GGC CTG TTC CTC

121 Ser Glu Gly Leu Lys Leu Val Asp Lys Phe Leu Glu Asp Val Lys Lys Leu Tyr His Ser
361 AGC GAG GGC CTG AAG CTA GTG GAT AAG TTT TTG GAG GAT GTT AAA AAG TTG TAC CAC TCA

141 Glu Ala Phe Thr Val Asn Phe Gly Asp Thr Glu Glu Ala Lys Lys Gln Ile Asn Asp Tyr
421 GAA GCC TTC ACT GTC AAC TTC GGG GAC ACC GAA GAG GCC AAG AAA CAG ATC AAC GAT TAC

161 Val Glu Lys Gly Thr Gln Gly Lys Ile Val Asp Leu Val Lys Glu Leu Asp Arg Asp Thr
481 GTG GAG AAG GGT ACT CAA GGG AAA ATT GTG GAT TTG GTC AAG GAG CTT GAC AGA GAC ACA
```

-continued

```
181 Val Phe Ala Leu Val Asn Tyr Ile  Phe Phe Lys Gly Lys Trp Glu Arg Pro Phe Glu Val
541 GTT TTT GCT CTG GTG AAT TAC ATC TTC TTT AAA GGC AAA TGG GAG AGA CCC TTT GAA GTC

Ala(b)
201 Lys Asp Thr Glu Glu Glu Asp Phe His Val Asp Gln Val Thr Thr Val Lys Val Pro Met
601 AAG GAC ACC GAG GAA GAG GAC TTC CAC GTG GAC CAG GTG ACC ACC GTG AAG GTG CCT ATG
                                                      BstEII

221 Met Lys Arg Leu Gly Met Phe Asn Ile  Gln His Cys Lys Lys Leu Ser Ser Trp. Val Leu
661 ATG AAG CGT TTA GGC ATG TTT AAC ATC CAG CAC TGT AAG AAG CTG TCC AGC TGG GTG CTG

Asn(c)
241 Leu Met Lys Tyr Leu Gly Asn Ala Thr Ala Ile  Phe Phe Leu Pro Asp Glu Gly Lys Leu
721 CTG ATG AAA TAC CTG GGC AAT GCC ACC GCC ATC TTC TTC CTG CCT GAT GAG GGG AAA CTA

261 Gln His Leu Glu Asn Glu Leu Thr His Asp Ile  Ile  Thr Lys Phe Leu Glu Asn Glu Asp
781 CAG CAC CTG GAA AAT GAA CTC ACC CAC GAT ATC ATC ACC AAG TTC CTG GAA AAT GAA GAC
                                           EcoRV

281 Arg Arg Ser Ala Ser Leu His Leu Pro Lys Leu Ser Ile  Thr Gly Thr Tyr Asp Leu Lys
841 AGA AGG TCT GCC AGC TTA CAT TTA CCC AAA CTG TCC ATT ACT GGA ACC TAT GAT CTG AAG

Val(a,c)
301 Ser Ile  Leu Gly Gln Leu Gly Ile  Thr Lys Val Phe Ser Asn Gly Ala Asp Leu Ser Gly
901 AGC ATC CTG GGT CAA CTG GGC ATC ACT AAG GTC TTC AGC AAT GGG GCT GAC CTC TCC GGG

321 Val Thr Glu Glu Ala Pro Leu Lys Leu Ser Lys Ala Val His Lys Ala Val Leu Thr Ile
961 GTC ACA GAG GAG GCA CCC CTG AAG CTC TCC AAG GCC GTG CAT AAG GCT GTG CTG ACC ATC

341 Asp Glu Lys Gly Thr Glu Ala Ala Gly Ala Met Phe Leu Glu Ala Ile  Pro |Met Ser| Ile
1021 GAC GAG AAA GGG ACT GAA GCT GCT GGG GCC ATG TTT TTA GAG GCC ATA CCC |ATG TCT| ATC

361 Pro Pro Glu Val Lys Phe Asn Lys Pro Phe Val Phe Leu Met Ile  Glu Gln Ana Thr Lys
1081 CCC CCC GAG GTC AAC TTC AAC AAA CCC TTT GTC TTC TTA ATG ATT GAA CAA AAT ACC AAG
            AvaI

381 Ser Pro Leu Phe Met Gly Lys Val Val Asn Pro Thr Gln Lys OC
1141 TCT CCC CTC TTC ATG GGA AAA GTG GTG AAT CCC ACC CAA AAA TAA CTGCCTCTCGCTCCTCAAC
                                       HinfI
                                 AAT CCC ACC CAA AAA TAG
                                     GGG TGG GTT TTT ATC AGCT
                                                        SalI 1201 CCCTCCCCTCCATCCCTGGCCCCCTCCCTGGATGACATTAAAGAAGGGTTGAGCTGGAAAAAAAAAAAAAAAAA
AAAAAA
```

LEGEND

Nucleotide and predicted amino acid sequences of $\alpha_1$-AT cDNA. The reactive center met-ser at positions 358-359 is boxed. Subscripts to amino acids in parentheses identify differences between the subject protein sequence and those derived from (a) protein sequencing (Carrell et al., 1982), (b) the cDNA of Woo et al., [see Carrell et al., 1982]), and (c) the cDNA of Bollen et al., 1983. The synthetic DNA molecules used in the construction of the BamHI to SalI fragment encoding the mature protein are shown as are the cDNA restriction sites used in this construction.

The above sequence was determined using the dideoxy sequencing method of Sanger et al., *Proc. Natl. Acad. Sci. USA* (1977) 74: 5463, in the M13 vectors of Messing et al., *Nucleic Acids Res.* (1981) 9: 309. The differences at the nucleotide and amino acid level from the published cDNA sequences are shown.

Construction of the full length clone for expression of yeast began with three fragments isolated from cDNA clones: 1) a 630 bp BamHI-BstEII fragment; 2) a 450 bp BstEII-AvaI fragment; and 3) and 85 bp AvaI-HinfI fragment. A synthetic adapter was employed having the following sequence:

$$A_2TC_3AC_3A_5TAG$$
$$G_3TG_3T_5ATCAGCT$$

Approximately two pmoles of fragments 1 and 2 were ligated together and after removal of the ligase, digested with BamHI and AvaI. Fragment 3 and the synthetic adapter were ligated and digested with AvaI and SalI and the two resulting fragment mixtures were ligated followed by digestion with BamHI and SalI. Fragments migrating upon electrophoresis in the region of about 1000–1400 bp were isolated and cloned by substitution into BamHI and SalI digested and alkaline phosphatase treated pBR322. The resulting plasmid is referred to as pATi.

Plasmid pPGAP (described previously in Example 10) was digested with NcoI, followed by blunt-ending, followed by SalI digestion and treatment with alkaline phosphatase. The NcoI-SalI fragment was substituted with an approximately 1250 bp blunt-ended (BamHI)-SalI fragment obtained from plasmid pATi, by BamHI digestion, blunt ending, and SalI digestion. This was inserted into the pPGAP vector to produce the plasmid pGAPATi, a 6.6 kb plasmid, which was digested with NcoI and BamHI and a 2.3 kb NcoI-BamHI fragment obtained having the $\alpha_1$-AT gene and the GAPDH terminator and approximately 400 bp BamHI-NcoI fragment obtained having the GAPDH promoter. These fragments were ligated together and inserted into the BamHI site of pC1/1. The plasmids pC1/1GAPATi8 and pC1/1GAPATi9 (ATCC Accession No. 20709) were obtained with the orientation of expression clockwise in the former and counterclockwise in the latter, with amp$^r$ being in the counterclockwise direction. These plasmids were transformed in *S. cerevisiae* AB103 (A.T.C.C. No. 20658, deposited Jan. 5, 1983) by standard methods, selecting for leucine prototrophy and grown as described above. Yeast extracts were prepared by lysis with glass beads and the $\alpha_1$-AT activity determined by inhibition of human leukocyte elastase.

Assays contained in 1 ml:0.1–0.2 human leukocyte elastase (HLE); 0.1 mM MeO-Suc-Ala-Ala-Pro-Val-p-nitroanilide (Beatty et al., J. Biol. Chem. (1980) 255: 3931); 50 mM Tris, pH 8, 0.5M NaCl, and the indicated amounts of yeast extract or human $\alpha_1$-AT. Assays were initiated by the addition of elastase, incubated at 28° C. for 15 min, terminated by the addition of 100 μl of 8N acetic acid and the absorbance at 410 nm determined. Typical results are shown in the following Table 5.

TABLE 5

| Plasmid | Strain | Amt. Extract (μl) | Amt. HLE (μg) | Amt. Protein (μg) | % Elastase Activity | % $\alpha_1$-AT* |
|---|---|---|---|---|---|---|
| pCl/1GAPATi8 | AB103 | 5.0 | 0.1 | 50.0 | 40 | 0.17 |
|  |  | 10.0 | 0.1 | 100.0 | 26 | 0.11 |
| pCl/1GAPATi9 | AB103 | 0.25 | 0.1 | 2.3 | 89 | 0.7 |
|  |  | 1.0 | 0.1 | 9.1 | 26 | 1.2 |
| pCl/1GAPATi9 | AB110 | 0.2 | 0.2 | 2.9 | 39 | 6.1 |
|  |  | 0.4 | 0.2 | 5.8 | 14 | 4.3 |

*Calculation based upon the Mol. wt. of HLE (29kD), the amount of protein added and the degree of inhibition.

The above data demonstrate that plasmids having the orientation of the expression cassette in the counter-clockwise orientation, the promoter proximal to the long sequence of pBR322, make 10–20 times more $\alpha_1$-AT than the same cassette in the other orientation.

Yeast strain AB110

Yeast strain 2150-2-3 was crossed with a yeast strain AB103 transformant containing pCl/1GAPATi9. The diploids were sporulated and the tetrads disected. Strains were maintained on leucine selective plates in order to ensure maintenance of the plasmid, since the parents are auxotrophs. A series of colonies were screened for their genotype with respect to a number of markers. The most vigorous strains were selected and cultures grown on leucine selective media. The best strain was designated AB110 (pCl/1GAPATi9), gave 6–7.5% of the total cell protein as $\alpha_1$-AT as shown in the above Table 3. The strain AB110 has the following genotype: Mat$\alpha$, ura3-52, leu2-04 or both leu2-3 and leu2-112, pep4-3, his4-580 (cir°).

EXAMPLE 13

Construction of PHO regulator, GAPDH promoter containing plasmids

Plasmid pPGT80 contains the sAg and 128 bp of 3' non-coding region under regulation of GAPDH promoter and and terminator (see Example 8). pPGT80 was digested with BamHI, the ends blunt-ended, followed by digestion with XbaI and the 500 bp fragment containing the GAPDH promoter and 5'-end of the sAg gene isolated.

The PHO5 gene was isolated from a yeast genomic library employing an oligonucleotide probe 5'-GGCACTCACACGTGGGACTAG-3' derived from the published partial sequence (Meyhack et al., The EMBO Journal (1982) 1: 675–680). A subfragment of this clone containing 550 bp of the 5'-untranslated region and approximately 80 bp of coding sequence was subcloned as a BamHI-SalI substitution in pBR322 to provide pPHO5. This fragment has the sequence 5'-ATGTTTAAA-3', encoding the first three amino acids, the second and third codons specifying an AhaIII site. The plasmid pHBS6 (described previously in Example 6) was digested with NcoI, blunt-ended, followed by digestion with BamHI and treatment with alkaline phosphatase. The PHO5 promoter region was obtained by digesting the bPHO5 plasmid with AhaIII, resecting the resulting fragment with Bal31 for a short time, followed by digestion with BamHI and isolation of a 500–550 bp BamHI blunt-ended fragment. This fragment was employed for substitution of the NcoI-BamHI fragment from pHBS6 and was screened for regeneration of the NcoI restriction site to provide plasmid pHBS6PHO5/1.

Plasmid pHBS6PHO5/1 was digested with BstEII which cleaves at position −175 in the PHO5 promoter. This molecule was blunt-ended, digested with SalI and the 650bp fragment having the 5'-portion of the promoter domain, containing 275 bp of pBR322 and 375 bp of the PHO5 promoter region isolated. This fragment was ligated with the blunt-ended (BamHI)-XbaI fragment obtained from digestion of pPGT80 with BamHI, blunt ending, followed by XbaI digestion. After digesting the ligated fragment with SalI and XbaI, the resulting fragment was then substituted into pPGT16-3 which had been digested with SalI and XbaI and treated with alkaline phosphatase. The resulting plasmid pPHO5PGT80 had a cassette comprising the PHO5 regulatory region, the GAPDH promoter, the sAg gene and the ADH terminator. This cassette was excised from the plasmid by BamHI digestion, whereby a 1.8 kb BamHI-BamHI fragment was gel isolated and ligated into the BamHI site of BamHI digested and alkaline phosphatase treated pCl/1 to provide plasmids PHO5-GAP1 (ATCC Accession No. 20707) and PHO5GAP2 where the PHO5 was distal and proximal to the long pBR322 sequence, respectively.

The two plasmids were transformed into yeast strain 2150-2-3 as described above and grown in rich media as described above for 8 to 10 generations in either high (7 mM) or low (0.2 mM) phosphate. Samples were harvested in late log phase and HBsAg determined as described previously. The results are shown below in Table 6.

TABLE 6

Regulation of HBsAg Production in Yeast using a Hybrid PHO5/GAPDH Promoter.

| Construction | High Phosphate (sAg μg/mg protein) (7 mM) | Low Phosphate (sAg μg/mg protein) (0.2 mM) | Induction low / high |
|---|---|---|---|
| PHO5GAP-1 | 0.08 | 0.95 | 12.0 |
| PHO5GAP-2 | 0.27 | 0.40 | 1.5 |

From the above results, it is evident that effective regulation with phosphate is obtained, with one orientation being superior to the other.

EXAMPLE 14

Use of Wild-type Promoter Regions and Hybrid Promoter Regions For Expression of Fused Peptides

Construction of pYSI1

A yeast expression plasmid pYSI1, containing the human SOD gene fused to the amino-terminus of human proinsulin gene, under the regulation of the GAP promoter and terminator was constructed. A triplet coding for methionine was included between the SOD and proinsulin genes to allow for chemical processing of the fusion protein. The SOD sequences correspond to a cDNA isolated from a human liver library, except for the first 20 codons which were chemically synthesized. The proinsulin sequence was chemically synthesized according to the amino acid sequence reported by (Bell et al. (1979), Nature 282: 525–527), but using yeast preferred codons. The GAP promoter and terminator sequences were obtained from the yeast GAP gene (Holland & Holland, J. Biol. Chem. (1979) 254: 5466–5474) isolated from a yeast library.

Plasmid pYSI1 was constructed as follows. Three fragments were employed which involve a 454 bp NcoI-Sau3A isolated from phSOD (also designated as pSODNco5, described in Example 11), where the fragment includes the entire coding sequence for human superoxide dismutase (hSOD) with the exception of the last three 3'-codons; a 51 bp Sau3A-HindIII synthetic adapter, which codes for the last three codons of hSOD, methionine, and the first 14 codons of proinsulin; and a 231 bp HindIII-SalI fragment, isolated from pINS5, which encodes proinsulin excepting the first 14 amino acids. These fragments were ligated together and introduced into the plasmid pPGAP (described in Example 10), which had been previously digested with NcoI and SalI and alkaline phosphatase treated. The resulting plasmid pSI1 was digested with BamHI to provide an expression cassette which was cloned into plasmid pC1/1 to yield pYSI1.

Plasmid phSOD (also designated as pSODNco5, described in Example 11) is a pBR322-derived bacterial expression vector which contains a complete cDNA coding (except that the first 20 codons were chemically synthesized) for hSOD as described in copending application Ser. No. 609,412 filed on May 11, 1984. Plasmid pINS5 is a pBR322-derived vector which contains a proinsulin coding sequence chemically synthesized according to the amino acid sequence reported by Bell et al., Nature (1979) 282: 525–527. Plasmid pPGAP is a pBR322-derived vector described in copending application 609,412 (supra) which contains a GAP promoter and GAP terminator (Holland and Holland, J. Biol. Chem. (1979) 254: 5466–5474) with a polylinker between them, which provides for single restriction sites for cloning. Plasmid pC1/1 is a yeast expression vector which includes pBR322 sequences, $2\mu$ plasmid sequences and the yeast gene LEU2 as a selectable marker. See EPO 83/306507.1, which relevant parts are incorporated herein by reference.

Construction of pYS12

To prepare the fused gene having the hSOD coding sequence at the 3'-terminus in the direction of transcription separated from the proinsulin gene by a "spacer" of codons coding for K-R-S-T-S-T-S, the following fragments were ligated. A 671 bp BamHI-SalI fragment containing the GAP promoter, the proinsulin gene and codons for the spacer amino acids; a 14 bp SalI-NcoI synthetic adapter, which codes for the last spacer amino acids as a junction of both genes; and a 1.5 kb NcoI-BamHI fragment isolated from pC1/1 GAPSOD described in copending application 609,412 (supra), which includes the hSOD coding region, 56 bp of hSOD terminator and 934 bp of GAP terminator region. The resulting cloned fragment was isolated and inserted into BamHI digested, alkaline phosphatase treated pC1/1.

Plasmids pPKI1 and pPKI2

Plasmids homologous to pYSI1 and pYSI2, but using the yeast pyruvate kinase (PYK) gene instead of hSOD gene, were also constructed. pPKI1 contains the PYK coding sequence fused to the amino-terminus of the human proinsulin gene under regulation of the yeast PYK promoter and yeast GAP terminator. pPKI2 contains the PYK coding sequence at the 3'-terminus in the direction of transcription separated from the proinsulin gene by a "spacer" of codons coding for K-R-S-T-S. This fused gene is under regulation of the GAP promoter and PYK terminator.

Construction of pYASI1

This yeast expression plasmid is similar to pYSI1 and contains the hSOD gene fused to the amino terminus of the human proinsulin gene, with a methionine codon at the junction between both genes. The fusion gene is under control of the hybrid inducible ADH2-GAP (yeast alcohol dehydrogenase 2) promoter and the GAP terminator. An about 3 kbp BamHI expression cassette was constructed by replacing the GAP promoter sequence from pYSI1 with the hybrid ADH2-GAP promoter sequence.

The ADH2 portion of the promoter was constructed by cutting a plasmid containing the wild type ADH2 gene (plasmid pADR2, see Beier and Young, Nature (1982) 300: 724–728) with the restriction enzyme EcoR5, which cuts at a position +66 relative to the ATG start codon, as well as in two other sites in pADR2, outside of the ADH2 region. The resulting mixture of a vector fragment and two smaller fragments was resected with Bal31 exonuclease to remove about 300 bp. Synthetic XhoI linkers were ligated onto the Bal31 treated DNA. The resulting DNA linker vector fragment (about 5 kb) was separated from the liners by column chromatography, cut with the restriction enzyme XhoI, religated and used to transform E. coli to ampicillin resistance. The positions of the XhoI linker additions were determined by DNA sequencing. One plasmid which contained an XhoI linker located within the 5' non-transcribed region of the ADH2 gene (position −232 from ATG) was cut with the restriction enzyme XhoI, treated with nuclease S1, and subsequently treated with the restriction enzyme EcoRI to create a linear vector molecule having one blunt end at the site of the XhoI linker and an EcoRI end.

The GAP portion of the promoter was constructed by cutting plasmid pPGAP (supra) with the enzymes BamHI and EcoRI, followed by the isolation of the 0.4 bp DNA fragment. The purified fragment was partially digested with the enzyme AluI to create a blunt end near the BamHI site.

Plasmid pJS104 was constructed by the ligation of the AluI-EcoRI GAP promoter fragment to the ADH2 fragment present on the linear vector described above.

Plasmid pJS104 was digested with BamHI (which cuts upstream of the ADH2 region) and with NcoI (which cuts downstream of the GAP region). The about 1.3 Kbp fragment containing the ADH2-GAP promoter was gel purified and ligated to an about 1.7 Kbp fragment containing the hSOD-proinsulin fusion DNA sequences and GAP terminator present in pYSI1 (previously described). This 3 Kbp expression cassette was cldoned into BamHI digested and phosphatase treated pC1/1 to yield pYASI1 (ATCC Accession No. 20745).

Expression of fusion proteins

Yeast strain 2150-2-3 (Mata, ade 1, leu 2-04, cir°) was transformed with the different vectors according to Hinnen et al., Proc. Natl. Acad. Sci. USA (1978) 75: 1929–1933. Single transformant colonies harboring constitutive GAP regulated vectors were grown in 2 ml of leu⁻ selective media to late log or stationary phase. Cells harboring inducible ADH2-GAP and regulated vectors were grown to saturation in leu⁻ selective media, subsequently diluted 1:20 (v/v) in YEP, 3% ethanol, and grown to saturation in this medium. Cells were lysed in the presence of SDS and reducing agent and the lysates clarified by centrifugation. Cleared lysates were subjected to polyacrylamide gel electrophoresis (Laemmli, Nature (1970) 277: 680). Following staining with Coomassie blue, a band of about 28kDal the size predicted for the fusion protein was observed in extracts from transformants containing the SOD-proinsulin fusion. This band was detected in those cells transformed with expression vectors, while being absent from extracts of cells harboring control (pC1/1) plasmids. The fusion protein accounts for over 10% of the total cell protein as estimated from the stained gels in those cells transformed with pYSI1, pYSI2 or pYASI1, while it accounts for less than 0.5% in pYPKI1 or pYPKI2 transformants. The following Table indicates the results:

| Plasmid | Description of sequences contained in the expression cassette.* | Expression percent of total cell protein |
|---|---|---|
| pYPKI 1 | PYK$_p$ PYK BCA5 GAP$_t$ | 0.5% |
| pYPKI 2 | GAP$_p$ M BCA5 KRSTS PYK PYK$_t$ | 0.5% |
| pYSI 1 | GAP$_p$ SOD M BCA5 GAP$_t$ | 10% |
| pYSI 2 | GAP$_p$ M BCA5 KR(ST)$_2$S SOD GAP$_t$ | 10% |
| pYASI 1 | (ADH2—GAP)$_p$ SOD M BCA5 GAP$_t$ | 10% |

Note:
Proinsulin accounts for less than 0.1% of total cell protein in cells transformed with pYGAPINS5, a plasmid containing the proinsulin gene under regulation of GAPH promoter and terminator (GAP$_p$ M BCA5 GAP$_t$).
*PYK: pyruvate kinase gene
SOD: human SOD gene
BCA5: proinsulin gene
M, K, R, S, T: one letter amino acid code
GAP$_p$: GAP promoter
GAP$_t$: GAP terminator
PYK$_p$: PYK promoter
PYK$_t$: PYK terminator
(ADH2—GAP)$_p$: hybrid ADH2—GAP promoter Results shown in the Table indicate that while expression levels of PYK-proinsulin fusion are comparable to those obtained with proinsulin alone (about 0.5% and 0.1%, respectively), the expression levels of hSOD-proinsulin are about 20 to 100 fold higher. The inducible ADH2-GAP hybrid transcriptional initiation regulatory region is preferred, since it is noted that constitutive production in scaled-up cultures results in unstable expression.

The hSOD-proinsulin proteins synthesized by yeast were also submitted to Western analysis. Cleared yeast lysates prepared as described above were electrophoresed on polyacrylamide gels (Laemmli, supra) and proteins were subsequently electroblotted onto nitrocellulose filters (Towbin et al., Proc. Natl. Acad. Sci. USA (1979) 76: 3450). Two identical filters were blotted. The filters were preincubated for 1 hr with 1% BSA in PBS and subsequently treated with rabbit anti-hSOD or guinea pig anti-insulin antibodies for 12 hr at 4° C. Both sera had been preadsorbed with pC1/1 control lysate in 10% goat serum. The filters were washed with 1% BSA PBS and a second goat anti-rabbit or anti-guinea pig antibody conjugated with horseradish peroxidase added. Finally, the filters were incubated with horseradish peroxidase color development reagent (Bio-Rad) and washed. The Western analysis showed that the fusion protein reacted with both antibodies.

EXAMPLE 15

Construction of pAB24/P. vivax 1-5 (FIG. 9a)

From a pUC9 vector (pUC9Ci) containing the P. vivax CS protein gene as a 4.1 kb fragment was isolated a BglII/XbaI fragment encoding all the repeat sequences (see Arnot et al., Science (1985) 230: 815). This gel purified fragment was then digested with FokI and BanI and the 5'-phosphorylated synthetic linkers of the following sequence were ligated. One linker provides for an NcoI site while the other provides a SalI overhang:

CCTTGGAACCATGG
GGAACCTTGGTACCGTCT

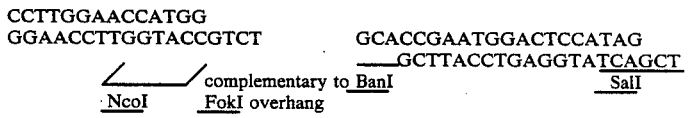

The linker containing fragment was digested with NcoI and SalI, isolated by gel electrophoresis and cloned into NcoI/SalI digested pBS100. pBS100 is a pBR322 derived plasmid containing the ADH2 regulated GAPDH promoter (1200 bp) and teh GAPDH terminator (900bp). The expression cassette was excised by digestion with BamHI, purified by gel electrophoresis and cloned into pAB24, a yeast vector.

pBS100 is a pBR322 derived plasmid containing the ADH2 regulated GAPDH promoter (about 1.2 bp) and the GAPDH terminator (about 900 bp). The BamHI-NcoI ADH-GAP promoter fragment was obtained from plasmid pJS103 (see below). The Sal-Bam GAP terminator fragment was derived from plasmid pPGAP (previously described in Example 10).

Plasmid pJS103 is the same as plasmid pJS104 (previously described under "Construction of pYASI1 in Example 14) except that the GAP fragment of the ADH-GAP promoter is about 200 bp in pJS103 and 400 bp in pJS104. Construction of pJS103 was the same as pJS104, except that during preparation of the GAP portion of the promoter, the 0.4 Kbp BamHI-EcoRI fragment was completely digested with AluI (instead of partial digestion for pJS104) and an about 200 bp fragment was isolated.

pAB24 is a yeast expression vector (FIG. 9*b*) which contains the complete 2$\mu$ sequences (Broach 1981. In: Molecular Biology of the Yeast Saccharomyces, 1: 445, Cold Spring Harbor Press) and pBR322 sequences. It also contains the yeast URA3 gene derived from plasmid YEp24 (Botstein, et al., *Gene* (1979) 8: 17) and the yeast $LEU2^d$ gene derived from plasmid pC1/1 (see EPO 116201). Insertion of the expression cassette was in the BamHI site of pBR322, thus interrupting the gene for bacterial Resistance to ampicillin.

Expression of *P. vivax* CS proteins

Yeast strain AB110 (Mat$\alpha$, leu2-04, or both leu2-3 and leu2-112, pep4-3, his4-580, cir°) was transformed with pAB24/*P. vivax*1-5 according to Hinnen, et al., *Proc. Natl. Acad. Sci. USA* (1978) 75: 1929–1933. Single transformant colonies harboring GAP regulated vectors were grown in 2 ml of leu$^-$ selective media to late log or stationary phase. Cultures were subsequently diluted 1:20 (v/v) in YEP, 1% glucose and grown to saturation (about 36 h) in this medium. Cells were lysed in the presence of SDS and reducing agent and the lysates clarified by centrifugation. Cleared lysates were subjected to polyacrylamide gel electrophoresis (Laemmli, *Nature* (1970) 277: 680). Following staining with Coomassie blue, a heavy band of about 38kDal was observed in extracts from transformants containing the *P. vivax* plasmid. This band was detected in those cells transformed with the expression vector, while being absent from extracts of cells harboring control (pCl/l) plasmids. The fusion protein accounts for over 10% of the total cell protein. The reason for abnormal cell migration (38kD) versus 23kD (predicted from DNA construction) may be related to anomalous SDS binding as previously reported for *P. Knowlesi* CS proteins (Ozaki, et al., *Cell* (1983) 34: 815).

To confirm the identity of the 38kD band, proteins synthesized by yeast were also submitted to Western analysis. Cleared yeast lysates prepared as described above were electrophoreses on polyacrylamide gels (Laemmli, supra) and proteins were subsequently electroblotted onto nitrocellulose filters (Towbin, et al., *Proc. Natl. Acad. Sci. USA* (1979) 76: 3450). The filter was preincubated for 1 h with 1% BSA in PBS and subsequently treated with a monoclonal antibody to *P. vivax* CS protein (obtained from F. Zavala and V. Nussenzweig, NYU) for 12 h at 4° C. The filters were washed with 1% BSA PBS and a second goat anti-mouse antibody conjugated with horseradish peroxidase added. Finally, the filters were incubated with horseradish peroxidase color development reagent (Bio-Rad) and washed. The Western analysis showed that the fusion protein reacted with the monoclonal antibodies.

The above results demonstrate the efficiency and utility of using the GAPDH and PyK transcriptional initiation regions in conjunction with the wild-type upstream regulatory region or regulatory regions from other promoters or prokaryotic enhancer regions. Thus, yeast systems are provided for the economic and efficient expression of a wide variety of naturally-occurring peptides as well as fused peptides. In addition, constitutive or inducible expression can be achieved.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising in order of transcription a first transcriptional regulatory region obtained from one of the yeast genes ADR3, GAL4, or the regulatory region of PHO5, which provides for inducible transcriptional regulation; a second transcriptional initiation region from the yeast GAPDH gene of FIG. 2; a structural gene coding for other than the wild-type gene of said transcriptional initiation region; and a terminator region.

2. A DNA construct according to claim 1, wherein induction results from a change in concentration of an organic or inorganic nutrient.

3. A DNA construct according to claim 1, wherein induction results from a change in temperature.

4. An expression vector comprising:

a yeast replication system;

and an expression cassette comprising in order of transcription a first transcriptional regulatory region obtained from one of the yeast genes ADR3, GAL4, or the regulatory region of PHO5, which provides for inducible transcriptional regulation in yeast;

a transcriptional initiation region from the yeast GAPDH gene of FIG. 2;

a structural gene coding for other than the wild-type gene of said transcriptional initiation region; and a terminator region.

5. An expression vector according to claim 4, wherein said first transcriptional regulatory region is inducible by changing concentration of an organic or inorganic nutrient.

6. An expression vector according to claim 4, wherein said first transcriptional regulatory region is inducible by a temperature change.

7. An expression vector according to claim 4, wherein said structural gene comprises the $\alpha$-secretory leader, processing signal and an open reading frame coding for a polypeptide of at least about 12 amino acids.

8. A yeast host having an episomal element according to claim 4.

9. A method for producing a polypeptide which comprises growing a yeast host according to claim 8 in an appropriate nutrient medium;

whereby the structural gene is expressed to produce said peptide.

10. A method according to claim 9, wherein said structural gene includes the $\alpha$-factor leader and processing signal, whereby said peptide is processed and secreted.

11. A method according to claim 9, wherein said peptide is retained in the cytoplasm of said yeast host, and including the additional steps of isolating said peptide from said yeast host.

12. A DNA construct comprising in order of transcription a first transcriptional regulatory region obtained from one of the yeast genes ADR3, GAL4, or the regulatory region of PHO5; a second transcriptional initiation region from the yeast GAPDH gene of FIG. 2; a structural gene coding for other than the wild-type gene of said transcriptional initiation region; and a terminator region, wherein said DNA construct is a linear fragment free of other DNA or joined to other DNA functional in a cellular host.

13. A DNA construct according to claim 12, wherein said other DNA includes a replication system functional in a prokaryotic host and/or yeast.

14. A DNA construct according to any of claims 12 or 13, wherein said structural gene includes at its 5' terminus α-factor leader sequence and processing signal.

15. A DNA construct according to claim 12, wherein said structural gene codes for at least an immunologically active fragment of a malarial circumsporozoite protein.

16. A DNA construct according to claim 12, wherein said structural gene codes for at least an immunologically active fragment of superoxide dismutase.

17. A DNA construct according to claim 12, wherein said structural gene codes for at least an immunologically active fragment of α1-antitrypsin or mutants thereof having enzyme inhibitory activity.

18. A DNA construct according to claim 12, wherein said structural gene codes for at least an immunologically active fragment of hepatitis B surface antigen.

19. A DNA construct according to claim 12, wherein said structural gene codes for at least an immunologically active fragment of insulin.

20. A DNA construct according to claim 12, wherein said structural gene codes for an SOD-insulin fusion product.

21. A transcriptional regulation control region comprising in the direction transcription:
   a transcriptional regulatory region obtained from one of the yeast genes GAL4, ADR3, or the regulatory region of PHO5; and
   a yeast transcription initiation region from the yeast glycolytic enzyme GAPDH shown in FIG. 2, wherein said transcriptional initiation region is joined through an untranslated region to a sequence encoding for alphafactor leader peptide and a processing signal joined to a structural gene in reading frame; and
   a DNA sequence functional in a yeast host, other than the wild-type gene of said transcription initiation region.

* * * * *